(12) United States Patent
Taylor et al.

(10) Patent No.: US 11,013,576 B2
(45) Date of Patent: May 25, 2021

(54) ARTICLES AND METHODS FOR PREPARING A SURFACE FOR OBTAINING A PATENT SAMPLE

(71) Applicant: OPKO Diagnostics, LLC, Woburn, MA (US)

(72) Inventors: Jason Taylor, Windham, NH (US); David Steinmiller, Menlo Park, CA (US); Hardeep Singh, Arlington, MA (US); Rebecca Wagner, Boulder, CO (US); Gary J. Fagan, Marblehead, MA (US); Vincent Linder, Tewksbury, MA (US)

(73) Assignee: OPKO Diagnostics, LLC, Woburn, MA (US)

( * ) Notice: Subject to any disclaimer, the term of this patent is extended or adjusted under 35 U.S.C. 154(b) by 0 days.

(21) Appl. No.: 15/535,665

(22) PCT Filed: Oct. 13, 2016

(86) PCT No.: PCT/US2016/056775
§ 371 (c)(1),
(2) Date: Jun. 13, 2017

(87) PCT Pub. No.: WO2017/066405
PCT Pub. Date: Apr. 20, 2017

(65) Prior Publication Data
US 2017/0367783 A1 Dec. 28, 2017

Related U.S. Application Data

(60) Provisional application No. 62/242,893, filed on Oct. 16, 2015.

(51) Int. Cl.
*A61B 90/80* (2016.01)
*A61B 5/15* (2006.01)
(Continued)

(52) U.S. Cl.
CPC .............. *A61B 90/80* (2016.02); *A61B 5/15* (2013.01); *A61B 5/15003* (2013.01);
(Continued)

(58) Field of Classification Search
CPC ...................................................... A61B 90/80
(Continued)

(56) References Cited

U.S. PATENT DOCUMENTS 4,472,291 A   9/1984  Rosano
4,548,807 A  10/1985  Westfall et al.
(Continued)

FOREIGN PATENT DOCUMENTS

CN      203090226 U    7/2013
CN      103494745 A    1/2014
(Continued)

OTHER PUBLICATIONS

Harvinder et al., Does needle size matter?, 2007, J Diabetes Sci. Technol., (5): 725-729. (Year: 2007).*
(Continued)

*Primary Examiner* — Holly Kipouros
(74) *Attorney, Agent, or Firm* — Wolf, Greenfield & Sacks, P.C.

(57) ABSTRACT

Articles and methods for preparing a surface for obtaining a patient sample, such as blood, are generally provided. In some embodiments, the methods involve wiping a surface of skin of a patient in preparation for obtaining a sample (e.g., a blood sample) from the patient. In some embodiments, the methods involve wiping the surface of the skin with two or more wipes. For instance, the surface of the skin may be wiped with a first wipe comprising a surfactant and a second wipe comprising an antiseptic solution. Advantageously, the use of a first wipe including a surfactant followed by a second wipe may remove a higher amount of certain con-
(Continued)

taminants (e.g., proteins, bacteria, viruses) from the surface of the skin as compared to the use of a single wipe or by hand-washing alone.

23 Claims, 6 Drawing Sheets

(51) Int. Cl.
| | |
|---|---|
| A61L 2/18 | (2006.01) |
| B08B 1/00 | (2006.01) |
| B08B 3/08 | (2006.01) |
| C11D 3/48 | (2006.01) |
| C11D 17/04 | (2006.01) |
| C11D 11/00 | (2006.01) |

(52) U.S. Cl.
CPC .. *A61B 5/150007* (2013.01); *A61B 5/150022* (2013.01); *A61B 5/150305* (2013.01); *A61L 2/186* (2013.01); *B08B 1/006* (2013.01); *B08B 3/08* (2013.01); *C11D 3/48* (2013.01); *C11D 11/0064* (2013.01); *C11D 17/049* (2013.01); *A61B 5/150343* (2013.01); *A61B 5/150358* (2013.01)

(58) Field of Classification Search
USPC .......................................................... 422/28
See application file for complete search history.

(56) References Cited

U.S. PATENT DOCUMENTS

| | | | |
|---|---|---|---|
| 4,793,988 | A | 12/1988 | Casey et al. |
| 5,021,185 | A | 6/1991 | Mustakallio |
| 5,122,365 | A | 6/1992 | Murayama |
| 5,178,157 | A | 1/1993 | Fanlo |
| 5,552,089 | A | 9/1996 | Misselyn et al. |
| 5,612,307 | A | 3/1997 | Chambers et al. |
| 5,650,384 | A | 7/1997 | Gordon et al. |
| 5,823,951 | A | 10/1998 | Messerschmidt |
| 5,914,177 | A | 6/1999 | Smith, III et al. |
| 5,978,466 | A | 11/1999 | Quattrocchi |
| 6,071,541 | A | 6/2000 | Murad |
| 6,123,966 | A | 9/2000 | Kross |
| 6,258,370 | B1 | 7/2001 | Behrends et al. |
| 6,342,208 | B1 | 1/2002 | Hyldgaard et al. |
| 6,413,921 | B1 | 7/2002 | Childers et al. |
| 6,502,699 | B1 | 1/2003 | Watson |
| 6,613,729 | B1 | 9/2003 | Cole et al. |
| 7,736,890 | B2 | 6/2010 | Sia et al. |
| 8,030,057 | B2 | 10/2011 | Linder et al. |
| 8,202,492 | B2 | 6/2012 | Linder et al. |
| 8,221,700 | B2 | 7/2012 | Steinmiller et al. |
| 8,222,049 | B2 | 7/2012 | Linder et al. |
| 8,287,461 | B2 | 10/2012 | MacDonald et al. |
| 8,309,538 | B2 | 11/2012 | Reilly |
| 8,501,416 | B2 | 8/2013 | Linder |
| 8,574,609 | B2 | 11/2013 | Lopes |
| 8,802,607 | B2 | 8/2014 | Fan et al. |
| 8,932,523 | B2 | 1/2015 | Linder et al. |
| 2002/0082177 | A1 | 6/2002 | Tabaac |
| 2003/0049866 | A1 | 3/2003 | Bushway et al. |
| 2005/0255235 | A1 | 11/2005 | Hiyoshi et al. |
| 2006/0094632 | A1* | 5/2006 | Horton, III ............ C11D 1/835 510/438 |
| 2006/0167380 | A1* | 7/2006 | Morton ................ A61B 10/007 600/573 |
| 2007/0016102 | A1 | 1/2007 | Askin |
| 2009/0075390 | A1 | 3/2009 | Linder et al. |
| 2010/0158756 | A1 | 6/2010 | Taylor et al. |
| 2011/0120562 | A1 | 5/2011 | Tan et al. |
| 2011/0159596 | A1 | 6/2011 | Keinan et al. |
| 2011/0190186 | A1 | 8/2011 | Collins |
| 2011/0253224 | A1 | 10/2011 | Linder et al. |
| 2011/0256551 | A1 | 10/2011 | Linder et al. |
| 2011/0312841 | A1* | 12/2011 | Silverbrook .......... B01L 3/5027 506/40 |
| 2012/0121679 | A1* | 5/2012 | Cannon ................. A61K 31/19 424/404 |
| 2013/0199946 | A1 | 8/2013 | Tennican |
| 2013/0273643 | A1 | 10/2013 | Vickers et al. |
| 2014/0272935 | A1 | 9/2014 | Dirckx et al. |
| 2015/0298128 | A1 | 10/2015 | Olsavsky et al. |

FOREIGN PATENT DOCUMENTS

| | | | |
|---|---|---|---|
| GB | 618 075 A | 2/1949 | |
| JP | 4213594 B2 | 1/2009 | |
| WO | WO-2007009092 A2 * | 1/2007 | ............. A61K 31/01 |
| WO | WO 2011/008581 A2 | 1/2011 | |

OTHER PUBLICATIONS

World Health Organization (WHO), Sample product dossier for WHO prequalification, 2014, pp. 1-116 (Year: 2014).*
Michigan Department of Community Health, Collection procedures for capillary blood lead samples, 2010, pp. 1-12 (Year: 2010).*
Barr et al., Capillary blood sampling, 2010, London Health Sciences Centre, pp. 1-35 (Year: 2010).*
Caldeira et al., Skin antiseptics in venous puncture-site disinfection for prevention of blood culture contamination: systematic review with meta-analysis, 2011, Journal of Hospital Infection, vol. 77, pp. 223-232 (Year: 2011).*
Choudhuri et al., Efficiency of skin sterilization for a venipuncture with the use of commercially available alcohol or iodine pads, 1990, American Journal of Infection Control, vol. 18 Issue 2, pp. 82-85 (Year: 1990).*
Michigan Regional Laboratory System, Hemoglobin Determination by Hemocue Analyzer, 2007, pp. 1-13 (Year: 2007).*
Koontongkaew et al., Amphiphilic property of chlorhexidine and its toxicity against *Streptococcus* mutans GS-5, 1994, The Journal of Nihon University School of Dentistry, vol. 36, pp. 235-240 (Year: 1994).*
Maddison et al., Small Animal Clinical Pharmacology, 2008, Saunders Elsevier, p. 552 (Year: 2008).*
Miano et al., Evaulation of a new, rapid, qualitative, one-step PSA Test for prostate cancer screening: the PSA RapidScreen test, 2005, Prostate Cancer and Prostatic Diseases, 8, pp. 219-223 (Year: 2005).*
PCT/US2016/056775, Jan. 10, 2017, International Search Report and Written Opinion.
International Search Report and Written Opinion for PCT/US2016/056775 dated Jan. 10, 2017.
Extended European Search Report for EP App. No. 16856160.3 dated Apr. 11, 2019.

* cited by examiner

ARTICLES AND METHODS FOR PREPARING A SURFACE FOR OBTAINING A PATENT SAMPLE

RELATED APPLICATIONS

The present application is the national phase of International Application No. PCT/US2016/056775 entitled "ARTICLES AND METHODS FOR PREPARING A SURFACE FOR OBTAINING A PATIENT SAMPLE", and filed on Oct. 13, 2016, and claims priority under 35 U.S.C. § 119(e) to U.S. application No. 62/242,893, filed Oct. 16, 2015 entitled, "ARTICLES AND METHODS FOR PREPARING A SURFACE FOR OBTAINING A PATIENT SAMPLE", which applications are hereby incorporated by reference to the maximum extent allowable by law.

TECHNICAL FIELD

The present invention generally relates to articles and methods for preparing a surface for obtaining a patient sample.

SUMMARY

The present invention generally relates to articles and methods for preparing a surface for obtaining a patient sample, such as a blood sample.

In one set of embodiments, a series of methods are provided. In one embodiment, a method for cleaning a surface of skin of a patient is provided. The method comprises wiping the surface with a first wipe, wherein the first wipe comprises a solution comprising a surfactant, and wherein the surfactant is present in the solution in an amount of between about 0.1 wt % and about 15 wt % of the solution. The method involves wiping at least a portion of the surface with a second wipe, wherein the second wipe comprises an antiseptic solution, and wherein the first and second wipes are different. The step of wiping at least a portion of the surface with the second wipe occurs after less than or equal to about 60 seconds of contacting the surface with the first wipe.

In another embodiment, a method for cleaning a surface of skin of a patient comprises applying a solution containing a surfactant to the surface of the skin, wherein the first wipe comprises a solution comprising a surfactant, and wherein the surfactant is present in the solution in an amount of between about 0.1 wt % and about 15 wt % of the solution, and wiping the surface of the skin with a first wipe. The method involves applying an antiseptic solution to the surface of the skin, and wiping at least a portion of the surface of the skin with a second wipe, wherein the first and second wipes are different. The step of wiping at least a portion of the surface with the second wipe occurs after less than or equal to about 60 seconds of contacting the surface with the first wipe.

In some embodiments involving any one of the methods described above and/or herein, the step of applying a solution containing a surfactant to the surface of the skin comprises the step of wiping the surface of the skin with the first wipe, which contains the solution containing the surfactant.

In some embodiments involving any one of the methods described above and/or herein, the step of applying an antiseptic solution to the surface of the skin comprises the step of wiping at least a portion of the surface of the skin with the second wipe, which contains the antiseptic solution.

In some embodiments involving any one of the methods described above and/or herein, prior to the first wiping step, the first wipe is substantially dry and/or prior to the second wiping step, the second wipe is substantially dry.

In some embodiments involving any one of the methods described above and/or herein, prior to the first wiping step, the first wipe is substantially wet and/or prior to the second wiping step, the second wipe is substantially wet.

In some embodiments involving any one of the methods described above and/or herein, the step of applying the surfactant to the surface of the skin occurs prior to the first wiping step.

In some embodiments involving any one of the methods described above and/or herein, the step of applying the antiseptic solution to the surface of the skin occurs prior to the second wiping step.

In another set of embodiments, a method for obtaining a blood sample from a patient is provided. The method comprises collecting the blood sample from the patient at a collection site, wherein within 1 minute of collecting the blood sample, a surface of the collection site was subjected to a first wiping step and a second wiping step. The first wiping step involves wiping the surface of the collection site with a first wipe. The first wipe comprises a surfactant. The second wiping step involves wiping at least a portion of the surface of the collection site with a second wipe. The second wipe comprises an antiseptic solution. The first and second wipes are different.

In another embodiment, a method for obtaining a blood sample from a patient comprises collecting the blood sample from the patient at a collection site, wherein within 1 minute of collecting the blood sample, a surface of the collection site was subjected to a step of exposing the surface to a solution comprising a surfactant, a first wiping step, a step of exposing the surface to an antiseptic solution, and a second wiping step. The first wiping step involves wiping the surface of the collection site with a first wipe. The second wiping step involves wiping at least a portion of the surface of the collection site with a second wipe. The first and second wipes are different.

In some embodiments involving any one of the methods described above and/or herein, prior to the first wiping step, the first wipe comprises the solution comprising the surfactant.

In some embodiments involving any one of the methods described above and/or herein, prior to the second wiping step, the second wipe comprises the antiseptic solution.

In some embodiments involving any one of the methods described above and/or herein, the step of exposing the surface to a solution comprising the surfactant and the first wiping step occur substantially simultaneously.

In some embodiments involving any one of the methods described above and/or herein, the step of exposing the surface to an antiseptic solution and the second wiping step occur substantially simultaneously.

In one set of embodiments, a kit is provided. In one embodiment, a kit comprises a first wipe comprising a first absorbent material and a solution absorbed therein. The solution comprises a surfactant present in an amount of between about 0.1 wt % and about 15 wt % of the solution. The kit also comprises a second wipe comprising a second absorbent material and an antiseptic solution absorbed therein. The first and second absorbent materials are the same or different. The first wipe and the second wipe are each enclosed in a different package, each package having a water permeability of less than or equal to about 0.05 gms H$_2$O/100 sq in/24 hours determined according to the standard ASTM D-1249 at 100 F, 90% relative humidity.

In another embodiment, a kit comprises a first wipe comprising a first absorbent material, a first solution comprising a surfactant present in an amount of between about 0.1 wt % and about 15 wt % of the solution, a second wipe, and an antiseptic solution. The first and second absorbent materials are the same or different. The first wipe and the second wipe are each enclosed in a different package, wherein at least one of the packages has a water permeability of less than or equal to about 0.05 gms H$_2$O/100 sq in/24 hours determined according to the standard ASTM D-1249 at 100 F, 90% relative humidity.

In some embodiments involving any one of the methods described above and/or herein, the first wipe comprises the solution comprising the surfactant.

In some embodiments involving any one of the methods described above and/or herein, the second wipe comprises the antiseptic solution.

In another set of embodiments, a packaged wipe is provided. The packaged wipe comprises an absorbent material, a solution absorbed in the absorbent material, wherein the solution comprises water and sodium dodecyl sulfate. Sodium dodecyl sulfate is present in the solution in an amount ranging between about 0.1 wt % and about 15 wt %. The absorbent material is enclosed in a package having a water permeability of less than or equal to about 0.05 gms H$_2$O/100 sq in/24 hours determined according to the standard ASTM D-1249 at 100 F, 90% relative humidity.

Other advantages and novel features of the present invention will become apparent from the following detailed description of various non-limiting embodiments of the invention when considered in conjunction with the accompanying figures. In cases where the present specification and a document Incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Articles and methods for preparing a surface for obtaining a patient sample, such as blood, are generally provided. In some embodiments, the methods involve wiping a surface of skin of a patient in preparation for obtaining a sample (e.g., a blood sample) from the patient. In some embodiments, the methods involve wiping the surface of the skin with two or more wipes. For instance, the surface of the skin may be wiped with a first wipe comprising a surfactant and a second wipe comprising an antiseptic solution.

Advantageously, the use of a first wipe including a surfactant followed by a second wipe may remove a higher amount of certain contaminants (e.g., proteins, bacteria, viruses) from the surface of the skin as compared to the use of a single wipe or hand-washing alone.

In some cases, the two or more wipes may be provided as a kit. For example, in some embodiments, the kit includes the two or more wipes and, optionally, a device for collecting the sample from the patient. Each of the disclosed wipes may be contained within a package (e.g., a water impermeable package) such that the wipes may be stored for a length of time before use.

As used herein, a "subject" or a "patient" refers to any mammal (e.g., a human), for example, a mammal that may be susceptible to a disease or bodily condition. Examples of subjects or patients include a human, a non-human primate, a cow, a horse, a pig, a sheep, a goat, a dog, a cat or a rodent such as a mouse, a rat, a hamster, or a guinea pig. Generally, the invention is directed toward use with humans. A patient may be a subject diagnosed with a certain disease or bodily condition or otherwise known to have a disease or bodily condition. In some embodiments, a patient may be diagnosed as, or known to be, at risk of developing a disease or bodily condition. In other embodiments, a patient may be suspected of having or developing a disease or bodily condition, e.g., based on various clinical factors and/or other data.

In some embodiments, a method described herein comprises wiping a surface (e.g., of skin) with a first wipe and, after a period of time, wiping at the surface with a second wipe. The term wipe as used herein generally refers to an article (e.g., an absorbent article) comprising a fluid which may be rubbed against a surface. The term wiping as used herein generally refers to the rubbing of a surface with an article such as a wipe. For example, as shown illustratively in FIG. 1A, a method 100 comprises a first wiping step 110 comprising wiping the surface with the first wipe, and a second wiping step 120 comprising wiping the surface with the second wipe. Generally, the second wiping step comprises wiping at least a portion of the surface wiped by the first wipe, with the second wipe. The second wipe is typically a different article than the first wipe, as described in more detail below.

Figure 1A:
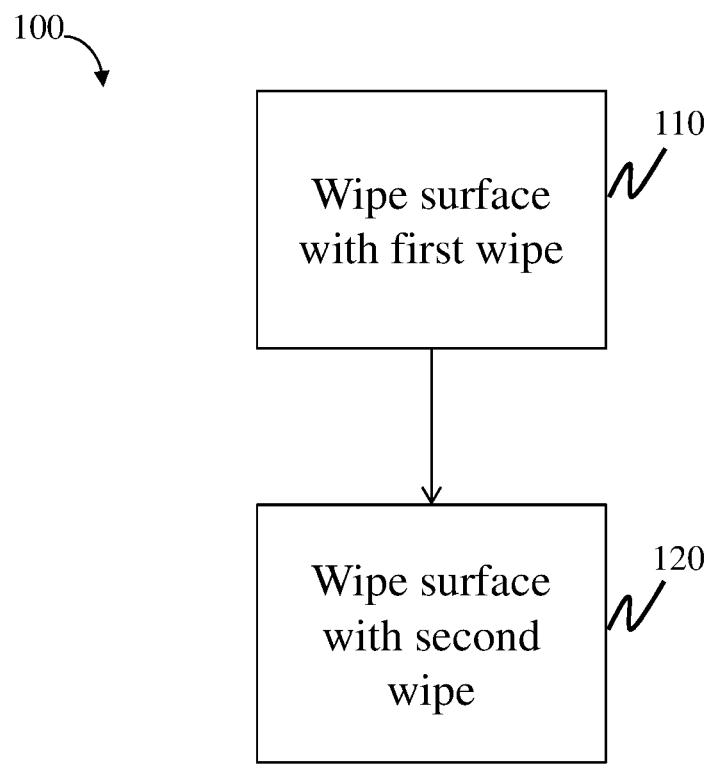
FIG. 1A is a flowchart of a method for wiping a surface, according to one set of embodiments.

It should be appreciated that while FIG. 1A (and FIG. 1B) shows to wiping steps, and other embodiments additional wiping steps (e.g., a third wiping step using a third wipe) may be performed. Additionally, while FIG. 1A (and FIG. 1B) shows a first wipe being used before a second wipe, in other embodiments the second wipe may be applied before the first wipe. Other configurations and procedures are also possible. It can be appreciated that the description herein with respect to first and second wipes may also apply to additional wipes (e.g., a "third wipe", a "fourth wipe", etc.).

In certain embodiments, the first wipe and second wipe are provided as a kit. For example, as shown illustratively in FIG. 1C, a kit 200 may comprise a first wipe 210 and a second wipe 220. The first and second wipes may be packaged independently in some instances. The kit may be used for carrying out a method described herein, e.g., involving a first wiping step comprising wiping a surface at a collection site with first wipe 210 and a second wiping step comprising wiping the surface with second wipe 220. In some embodiments, the kit comprises two or more, three or more, or four or more wipes (e.g., for the third wiping step, etc., not shown).

Figure 1B:
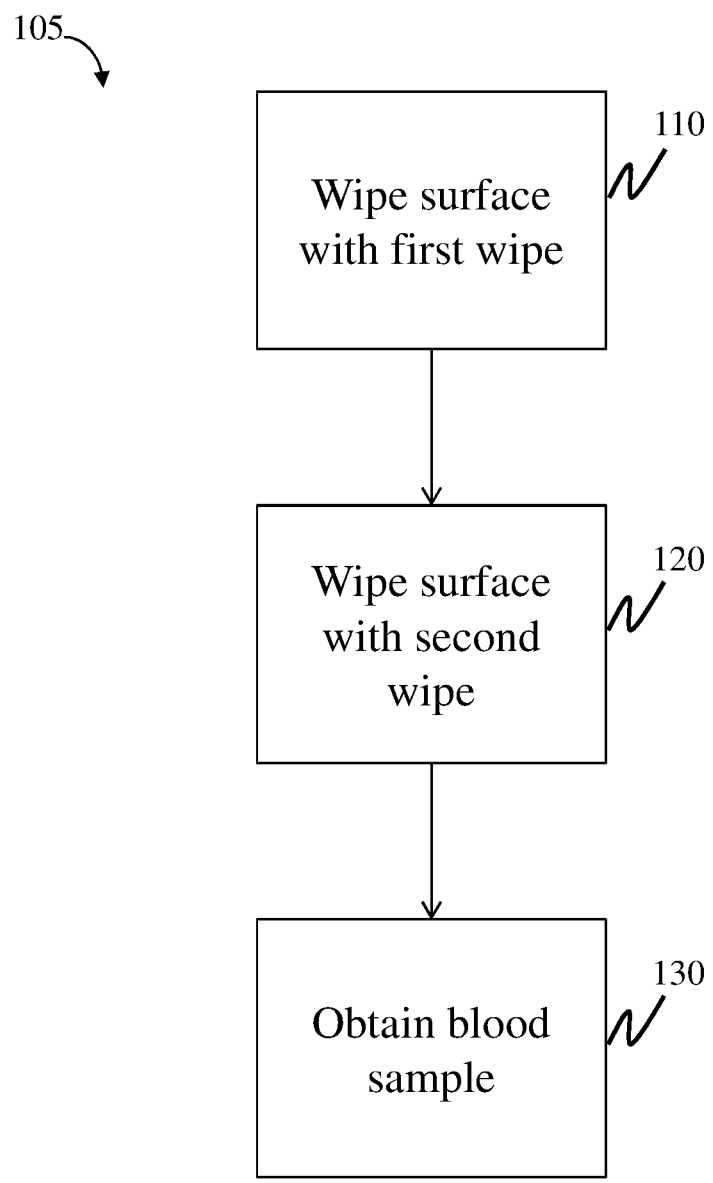
FIG. 1B is a flowchart of a method for preparing a surface for collecting a blood sample, according to one set of embodiments.
Figure 1C:
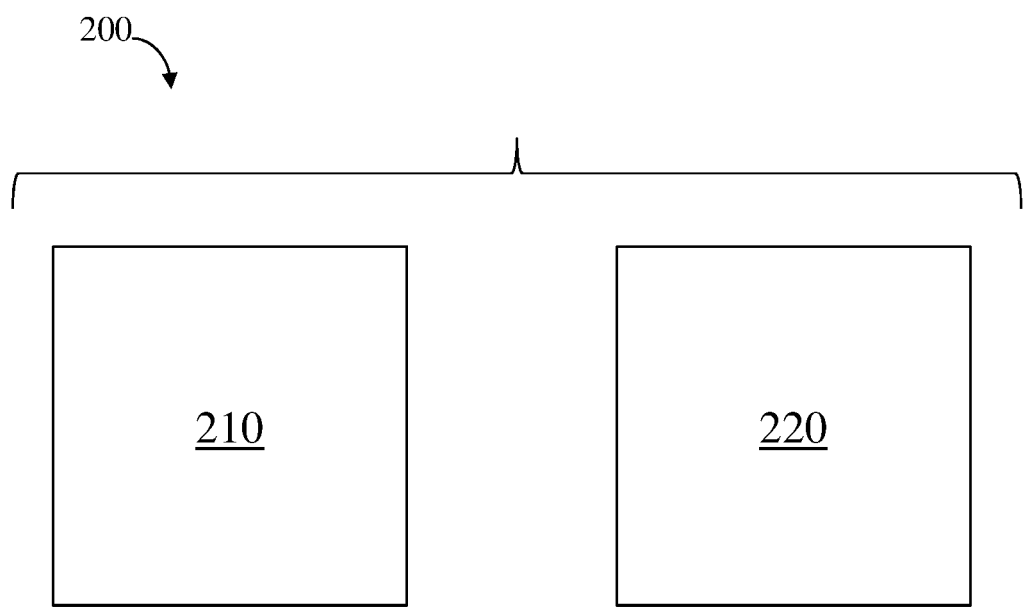
FIGS. 1C-1D are schematic diagrams of exemplary kits comprising at least one wipe, according to one set of embodiments.

In some embodiments, the method comprises obtaining a biological sample after wiping with at least the first wipe and the second wipe. For example, as illustrated in FIG. 1B, a method 105 includes a third step 130 comprising obtaining a biological sample may occur after second wiping step 120. In certain embodiments, the biological sample is collected from a location on the surface that has been wiped by both the first wipe and the second wipe prior to collecting the biological sample. In an illustrative example, a surface of skin located on a patient's finger may be wiped with a first wipe, at least a portion of the surface of the skin located on the patient's finger may be wiped with a second wipe, and then a biological sample may be collected from the location within the portion of the surface of the skin located on the patient's finger that was wiped with both wipes.

Figure 1D:
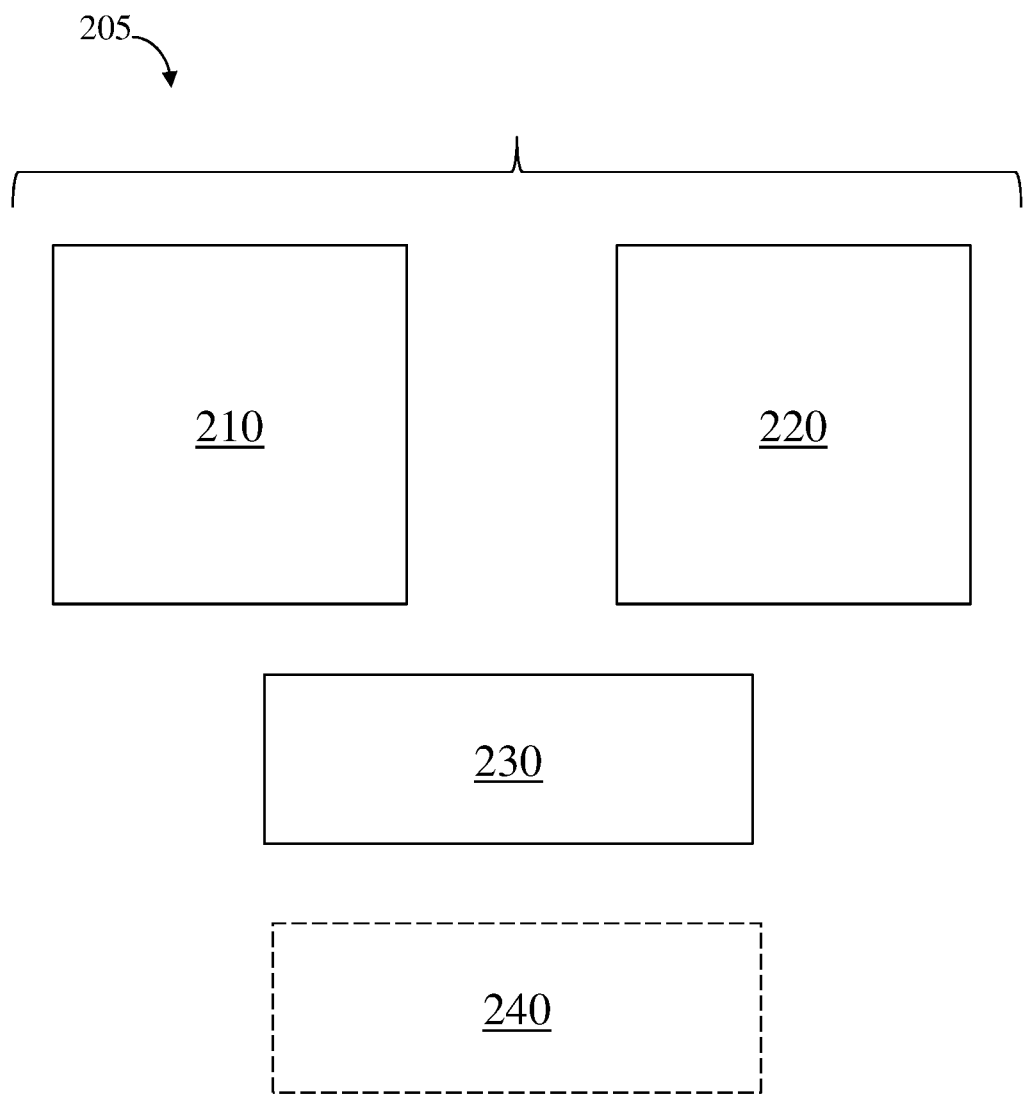

In some embodiments, a kit comprises a (micro)fluidic component for collecting the biological sample. For example, as illustrated in FIG. 1D, a kit 205 comprises first wipe 210, second wipe 220, and a (micro)fluidic component 230 for collecting a biological sample. Optionally, the kit may further include a microfluidic device 240 for analyzing a sample component. (Micro)fluidic components for collecting biological samples and microfluidic devices for analyzing a sample component are described in more detail below.

Wiping a surface of skin with the first wipe and the second wipe may offer several advantages as compared to wiping the surface of skin with a single wipe and/or no wipe, including, significantly increasing the amount of contaminants such as proteins (e.g., antigens), bacteria, and/or viruses, removed from the surface of the skin. Examples of proteins that may be removed from the wiping steps include prostate specific antigen (PSA), such as free prostate specific antigen (fPSA), intact prostate specific antigen (iPSA), total prostate specific antigen (tPSA) and human kallikrein 2 (hK2). In some embodiments, the contaminant is homologous with free-PSA. For example, in an exemplary embodiment, a PSA assay (e.g., a total prostate specific antigen (tPSA) assay) may be used to determine the amount of PSA protein removed from the surface of skin (e.g., which may contaminate and/or be present within a biological sample collected from that location on the surface of the skin).

Advantageously, wiping the surface of the skin with the first wipe and the second wipe significantly increases the amount of PSA protein removed from the surface of the skin and/or in the collected biological sample as compared to wiping the surface of the skin with a single wipe and/or no wipe. Total PSA assays are known in the art and generally comprise determining the concentration of PSA present in a collected biological sample from a patient from a location that, in some cases, has not been wiped, has been wiped with a single wipe, or has been wiped with a first wipe and a second wipe, as described herein. As determined herein, the amount of PSA present in the biological sample (e.g., before or after wiping) is determined using a Roche Elecsys™ total PSA assay. For example, blood samples may be spun down to plasma and the amount of PSA may be measured using the Roche Elecsys™ total PSA assay. Other assays such as Sangia™ tPSA assay, AutoDELFIA ProSTATUS™ assay, ELISA can also be used.

Additional examples of contaminants that may be removed from a sample collection surface (e.g., skin) using the articles and methods described herein include, for example, one or more components (e.g., proteins, hormones, antibodies) from a bodily fluid or bodily excretion such as sweat, semen, urine, tears, seminal fluid, vaginal secretion, mucus, and/or feces. In some embodiments, one or more diagnostic blood markers found in a bodily fluid or bodily excretions, or otherwise present at the sample collection site can be removed. In some embodiments, the component is found in a substance applied to or near the sample collection site. For example, a hormone such as testosterone applied topically to the skin (e.g., by a therapeutic cream, gel, patch, or the like) may be removed using the articles and methods described herein. Removal of topical testosterone from a sample collection site may be desirable prior to obtaining a sample for performing a testosterone assay. Similarly, removal of seminal fluid, which contains PSA, may be desirable prior to obtaining a sample for performing a PSA assay. In some embodiments, it may be especially desirable to remove such contaminants when the sample collection site is a skin surface that is susceptible to housing such contaminants. In general, a contaminant that may be removed or targeted for removal may be one that may affect the outcome of an assay and/or interfere with the determination of a target molecule, and which may be present at sample collection site.

A method may involve removing a component that would otherwise contaminate a biological sample, and therefore skew the results of, a subsequent analysis (e.g., an assay) to be performed with the biological sample. Removal of other contaminants are also possible.

Referring again to FIG. 1A, first wiping step 110 and second wiping step 120 may be separated by any suitable period of time (e.g., less than about 60 seconds). In some embodiments, the second wiping step occurs less than or equal to about 5 minutes, less than or equal to about 2 minutes, less than or equal to about 60 seconds, less than or equal to about 45 seconds, less than or equal to about 30 seconds, less than or equal to about 15 seconds, less than or equal to about 10 seconds, or less than or equal to about 1 second after the first wiping step. In certain embodiments, the second wiping step occurs at least about 1 second, at least about 5 seconds, at least about 10 seconds, at least about 15 seconds, at least about 30 seconds, at least about 45 seconds, or at least about 60 seconds after the first wiping step. Combinations of the above referenced ranges are also possible (e.g., between 1 second and 2 minutes, between 1 second and 60 seconds, between 30 seconds and 60 seconds, between 45 seconds and 2 minutes). Other ranges are also possible.

As described herein, in some embodiments, a first wiping step comprises wiping a surface of the collection site (e.g., skin) with a first wipe comprising a first solution (e.g., a surfactant solution). In other embodiments, the first wipe need not necessarily contain a solution; however, the solution may be packaged separately from the first wipe. For example, a kit may include first and second wipes packaged separately and a first solution packaged separately (e.g., in a bottle, capsule or other suitable container). In use, a first wiping step may comprise applying the first solution (e.g., a surfactant solution) to a surface of the collection site (e.g., by spraying, dipping, pouring, etc. the solution onto the collection site) and subsequently wiping the surface of the collection site with the first wipe. The first wipe may be substantially dry or substantially wet (e.g., containing the first solution, or a different solution such as water).

In some embodiments, the second wiping step comprises wiping a surface of the collection site (e.g., skin) with a second wipe comprising a second solution (e.g., an antiseptic solution). In other embodiments, the second wipe need not necessarily contain a solution; however, the solution may be packaged separately from the second wipe. For example, a kit may include first and second wipes packaged separately and a second solution (e.g., an antiseptic solution) packaged separately (e.g., in a bottle, capsule or other suitable container). In use, the second wiping step may comprise applying a second solution (e.g., an antiseptic solution) to a surface of the collection site (e.g., by spraying, dipping, pouring, etc. the solution onto the collection site) and subsequently wiping the surface of the collection site with the second wipe. The second wipe may be substantially dry or substantially wet (e.g., containing the second solution, or a different solution such as water).

In an exemplary embodiment, a step of exposing the surface to a solution comprising the surfactant and a first wiping step may occur substantially simultaneously, and/or a step of exposing the surface to an antiseptic solution and a second wiping step occur substantially simultaneously. For instance, the first wiping step may comprise wiping a surface of the skin with a first wipe comprising a first solution and/or the second wiping step may comprise wiping a surface of the skin with a second wipe comprising a second solution.

In another exemplary embodiment, the first wiping step comprises applying a first solution to a surface of the skin and subsequently wiping the surface of the skin with the first wipe and the second wiping step comprises wiping a surface of the skin with a second wipe comprising a second solution.

In certain embodiments, the first wiping step and the second wiping step are separated by a period of time such that a fluid (e.g., a surfactant solution) retained on the surface of the collection site (e.g., skin) after wiping with the first wipe substantially evaporates prior to wiping with the second wipe. Wiping the surface with the second wipe may remove any residual fluid or components therein retained on the surface of the collection site after wiping with the first wipe. For example, contaminants (e.g., PSA, testosterone) may be removed from the surface of the collection site. An assay, such as a tPSA assay (e.g., Roche Elecsys™ total PSA assay), as described herein, may be used, in some embodiments, to determine if the second wipe substantially removed contaminants (e.g., PSA, testosterone) from the surface of the collection site such that the contaminants are not included in a biological sample collected from the patient.

Additionally or alternatively, the second wipe may also be used to remove one or more active agents, or other components, from or contained in the first wipe. For example, a surfactant solution (detergent) retained on the surface of the collection site (e.g., skin) after wiping with the first wipe may be removed using the second wipe. In some embodiments, removal of such agents may desirable because their presence on the surface of sample collection site may interfere with the sample collection process. For example, a detergent present in the first wipe may remain at the sample collection site after applying the first wipe and may change the surface chemistry at the sample collection site, e.g., it may cause the sample collection site to become more hydrophilic. If a sample (e.g., a droplet of blood) is obtained at the sample collection site (e.g., skin of a finger), the sample may run off the sample collection site due to the greater hydrophilicity, and may therefore be difficult to collect. By wiping the sample collection with the second wipe after the first wipe, the detergent may be removed prior to forming a droplet of blood, thereby facilitating collection of the sample.

In some embodiments, a majority of a contaminant (e.g., a protein such as PSA protein) is removed from the surface of the collection site after the first and second wiping steps as compared to the amount of the contaminant (e.g., the protein such as PSA protein) present on the surface before the first and second wiping steps (e.g., as determined by an assay, such as a tPSA assay described herein). In certain embodiments, at least about 80%, at least about 85%, at least about 90%, at least about 95%, at least about 97%, at least about 98%, or least about 99% of a contaminant (e.g., a protein such as PSA protein) is removed from the surface of the collection site after the first and second wiping steps as compared to the amount of the contaminant (e.g., PSA protein) present on the surface before the first and second wiping steps. In some cases, substantially all of a contaminant is removed. In certain embodiments, 100% of the contaminant is removed. In other embodiments, less than 100%, less than or equal to about 99%, 98%, 97%, 96%, or 95% of the contaminant is removed. Combinations of the above-referenced ranges are also possible.

In some embodiments, the first wipe (and/or the second wipe) comprises a surfactant.

The term "surfactant," as used herein, is given its ordinary meaning in the art and refers to compounds having an amphiphilic structure which gives them a specific affinity for oil/water-type and water/oil-type interfaces which helps the compounds to reduce the free energy/surface energy of these interfaces. The term surfactant encompasses cationic surfactants, anionic surfactants, amphoteric surfactants, nonionic surfactants, zwitterionic surfactants, and mixtures thereof. In some embodiments, the surfactant is a nonionic surfactant. Nonionic surfactants generally do not contain any charges. Amphoteric surfactants generally have both positive and negative charges, however, the net charge of the surfactant can be positive, negative, or neutral, depending on the pH of the solution. Anionic surfactants generally possess a net negative charge. Cationic surfactants generally possess a net positive charge. Zwitterionic surfactants are generally not pH dependent. A zwitterion is a neutral molecule with a positive and a negative electrical charge, though multiple positive and negative charges can be present.

As noted above, a surfactant may be used to reduce the surface energy of an interface (e.g., an oil/water interface) at a collection site. The term surface energy, as used herein, is given its ordinary meaning in the art and refers to the extent of disruption of intermolecular bonds that occur when the surface is created (e.g., the energy excess associated with the surface as compared to the bulk). Generally, surface energy is also referred to as surface tension (e.g., for liquid-gas interfaces) or interfacial tension (e.g., for liquid-liquid interfaces). As will be understood by those skilled in the art, surfactants generally orient themselves across the interface to minimize the extent of disruption of intermolecular bonds (i.e. lower the surface energy). Typically, a surfactant at an interface between polar and non-polar phases orient themselves at the interface such that the difference in polarity is minimized.

In some embodiments, a particular surfactant may be selected depending on the desired contaminant to be removed from the surface of the collection site. For instance, if a contaminant to be removed has a net negative charge (or net positive charge), a positively charged (or negatively charged) surfactant may be included in the wipe.

In some embodiments, a detergent may remove a dried protein or other component from a surface of the collection site. Once dried onto a surface, a protein may be slow to be solubilized. A detergent may be used to aid in dissolution or solubilization of the dried protein on the surface for removal with a the wipe.

In some cases, a particular surfactant known to denature the contaminant of interest may be used (e.g., a denaturing detergent). As described herein, denaturation of a contaminant is determined by applying the surfactant to the contaminant (such as free-PSA) and determining the immunoreactivity of the contaminant by exposing the contaminant to an antibody to the contaminant (such as anti-PSA antibody). If the contaminant has been denatured, the antibody will not substantially bind to the contaminant. Those skilled in the art could determine denaturation of a protein by, for example, determining binding with an appropriate antibody by any suitable method, including an immunofluorescence assay.

In some embodiments, a detergent is chosen for both its ability to dissolve/solubilize and denature a contaminant of interest.

In certain embodiments, the surfactant is a soap. For example, in some embodiments, the soap is a castile soap. In certain embodiments, the soap is a derivative of fatty acid. Non-limiting examples of suitable fatty acids from which the soap may be derived include lauric acid, myristic acid, palmitic acid, stearic acid, oleic acid, linoleic acid, and linolenic acid. In some embodiments, the fatty acids are derived from natural fats including, for example, tallow, coconut oil, palm kernel oil, laurel oil, olive oil, and canola oil. Those skilled in the art would be capable of selecting suitable soaps based upon the teachings of this specification.

In some embodiments, the surfactant is a detergent. The term detergent generally refers to a surfactant or a mixture of surfactants with cleaning properties in dilute solutions. In some embodiments, the detergent is an anionic detergent such as alkylbenzenesulfonates, a cationic detergent such as a quaternary ammonium detergent, or a non-ionic detergent such as ethoxylates such as Tween and Triton. In some embodiments, the detergent is a lauryl sulfate. Non-limiting examples of lauryl sulfates include sodium lauryl sulfate (i.e. sodium dodecyl sulfate (SDS)), ammonium lauryl sulfate, and potassium lauryl sulfate. Other detergents are also possible and those skilled in the art would be capable of selecting suitable detergents based upon the teachings of the specification.

In some embodiments, the first wipe (and/or second wipe) comprises a solution comprising the surfactant. The surfactant may be present in the solution in any suitable amount. In some embodiments, the surfactant is present in the solution in an amount ranging between about 0.1 wt % and about 20 wt % versus the total weight of the solution. In some embodiments, the surfactant is present in the solution in an amount of at least about 0.1 wt %, at least about 0.2 wt %, at least about 0.5 wt %, at least about 1 wt %, at least about 2 wt %, at least about 3 wt %, at least about 5 wt %, at least about 7 wt %, at least about 10 wt %, at least about 15 wt %, or at least about 18 wt % versus the total weight of the solution. In certain embodiments, the surfactant is present in the solution in an amount of less than or equal to about 20 wt %, less than or equal to about 18 wt %, less than or equal to about 15 wt %, less than or equal to about 10 wt %, less than or equal to about 7 wt %, less than or equal to about 5 wt %, less than or equal to about 3 wt %, less than or equal to about 2 wt %, less than or equal to about 1 wt %, less than or equal to about 0.5 wt %, or less than or equal to about 0.2 wt %. Combinations of the above-referenced ranges are also possible (e.g., between about 0.1 wt % and about 20 wt %, between about 0.2 wt % and about 5 wt %, between about 1 wt % and about 3 wt %, between about 5 wt % and about 15 wt %). Other weight percents and surfactants are also possible. In some embodiments, the solution comprises a mixture of two or more surfactants present in the solution, each of the surfactants being present in the solution in one or more ranges described above (e.g., between about 0.1 wt % and about 10 wt %).

In some embodiments, other compounds or components may be present in the first and/or second wipe. For instance, hydrophobic compounds and/or hydrophilic compounds may be included. Non-limiting examples of additional compounds or components include denaturing agents (e.g., comprising urea and/or guanidinium), organic solvents, and oils (or grease).

In some embodiments, the second wipe (and/or first wipe) comprises an antiseptic (e.g., an antiseptic solution). The antiseptic may include, for example, an active antiseptic agent, optionally present in (e.g., dissolved in, dispersed in, solvated in, mixed with) a medium (e.g., a fluid, such as water). Non-limiting examples of active antiseptic agents suitable as antiseptics include quaternary ammonium compounds (e.g., benzalkonium chloride), alcohols (e.g., ethyl alcohol, isopropyl alcohol), chlorohexidines, antibacterial dyes (e.g., triphenylmethane), peroxides (e.g., hydrogen peroxide, benzoyl peroxide), permanganates (e.g., potassium permanganate), halogenated phenol derivatives (e.g., chloroxylenol, triclosan), quinolone derivatives (e.g., hydroxyquinoline sulphate), iodine (e.g., povidone-iodine), bleach, and the like. In an exemplary embodiment, the antiseptic comprises an isopropyl alcohol. In certain embodiments, the antiseptic comprises a mixture of two or more active antiseptic agents (e.g., a first alcohol and a second alcohol, an alcohol and a quaternary ammonium compound).

In certain embodiments, an active antiseptic agent may be present in both the first wipe and the second wipe. In some such embodiments, if an active antiseptic agent is present in the first wipe, it may be the same or different as the active antiseptic agent present in the second wipe, and may be present in the wipe(s) (e.g., first and/or second wipe) in any suitable amount as described herein.

An active antiseptic agent may be present in a solution of a wipe (e.g., in the antiseptic solution, or in the surfactant solution) in any suitable amount. In some embodiments, the active antiseptic agent (e.g., iodine) is present in the solution in an amount ranging between about 0.01 wt % and about 7 wt % versus the total weight of the solution. In some embodiments, the active antiseptic agent is present in the solution in an amount of at least about 0.01 wt %, at least about 0.02 wt %, at least about 0.05 wt %, at least about 0.1 wt %, at least about 0.5 wt %, at least about 1 wt %, at least about 2 wt %, at least about 3 wt %, or at least about 5 wt %. In certain embodiments, the active antiseptic agent is present in the solution in an amount of less than or equal to about 7 wt %, less than or equal to about 5 wt %, less than or equal to about 3 wt %, less than or equal to about 2 wt %, less than or equal to about 1 wt %, less than or equal to about 0.5 wt %, less than or equal to about 0.1 wt %, less than or equal to about 0.05 wt %, or less than or equal to about 0.02 wt %. Combinations of the above-referenced ranges are also possible (e.g., between about 0.01 wt % and about 10 wt %, between about 0.02 wt % and about 0.5 wt %, between about 0.1 wt % and about 5 wt %, between about 1 wt % and about 3 wt %, between 3 wt % and about 7 wt %). Other ranges are also possible. In some embodiments, a solution of a wipe comprises a mixture of two or more active antiseptic agents present in the solution, each of the active antiseptic agents being present in the solution in one or more ranges described above.

In certain embodiments, an active antiseptic agent (e.g., alcohol) is present in the solution in an amount ranging between about 30 wt % and about 80 wt % versus the total weight of the solution. In some embodiments, the active antiseptic agent is present in the solution in an amount of at least about 30 wt %, at least about 40 wt %, at least about 50 wt %, at least about 60 wt %, or at least about 70 wt %. In certain embodiments, the active antiseptic agent is present in the solution in an amount of less than or equal to about 80 wt %, less than or equal to about 70 wt %, less than or equal to about 60 wt %, less than or equal to about 50 wt %, or less than or equal to about 40 wt %. Combinations of the above-referenced ranges are also possible (e.g., between about 30 wt % and about 80 wt %, between about 50 wt % and about 80 wt %, between about 60 wt % and about 70 wt %). Other ranges are also possible.

In some embodiments, the antiseptic (e.g., antiseptic solution) comprises one or more additives. Non-limiting examples of suitable additives include colorants (e.g., dyes), odorants (e.g., perfumes), emulsifiers, and soothing agents (e.g., creams). In certain embodiments, the one or more additives do not have a substantial effect on the antiseptic agent functionality.

In certain embodiments, the antiseptic solution may optionally comprise a surfactant (e.g., in addition to an active antiseptic agent). In some such embodiments, if a surfactant is present in the antiseptic solution, it may be the same or different as the surfactant present in the surfactant solution of the other wipe, and may be present in the wipe (e.g., first and/or second wipe) in any suitable amount as described herein.

While the first and/or second wipe may include a surfactant in some cases, in some embodiments a first wipe (used for a first wiping step) may include a surfactant in a greater amount than that of a second wipe (used for a second wiping step). In certain embodiments, the first wipe includes at least 10%, at least 50%, at least 100%, at least 20%, at least 500%, or at least 1000% more surfactant than that of the second wipe. In one particular set of embodiments, the first wipe includes one or more surfactants, and the second wipe does not include any surfactant. For instance, in some cases the wipe used for wiping a surface of a collection site just prior to sample collection does not include any surfactant in some embodiments, or includes surfactant in a lesser extent (e.g., at least 10%, at least 50%, at least 100%, at least 20%, at least 500%, or at least 1000% less) than that of any previous wipe. Other configurations are also possible.

In some embodiments, the wipe (e.g., the first wipe, the second wipe) may include a suitable liquid (e.g., a surfactant solution, an antiseptic solution, a buffer, and combinations thereof), which may be used a solvent for components in the wipe. The liquid may be aqueous (water) based, and may include, for example, a buffer. Non-limiting examples of suitable buffers include phosphate, carbonate, acetate, zwitterionic buffers, borate, tris(hydroxymethyl)aminomethane, citrate, and malonate. In some cases, the liquid includes an alcohol. In other embodiments, the wipe (e.g., the first wipe, the second wipe) may be substantially dry.

Any suitable volume of liquid (e.g., a surfactant solution, an antiseptic solution, a buffer, and combinations thereof) may be contained in the wipe. In some embodiments, the wipe contains at least about 100 microliters per cubic centimeter, at least about 150 microliters per cubic centimeter, at least about 200 microliters per cubic centimeter, at least about 250 microliters per cubic centimeter, at least about 300 microliters per cubic centimeter, at least about 350 microliters per cubic centimeter, at least about 400 microliters per cubic centimeter, or at least about 450 microliters per cubic centimeter of wipe. In certain embodiments, the wipe contains less than or equal to about 500 microliters per cubic centimeter of wipe, less than or equal to about 450 microliters per cubic centimeter, less than or equal to about 400 microliters per cubic centimeter, less than or equal to about 350 microliters per cubic centimeter, less than or equal to about 300 microliters per cubic centimeter, less than or equal to about 250 microliters per cubic centimeter, less than or equal to about 200 microliters per cubic centimeter, or less than or equal to about 150 microliters per cubic centimeter of wipe. Combinations of the above referenced ranges are also possible (e.g., between about 100 microliters per cubic centimeter and about 500 microliters per cubic centimeter, between about 100 microliters per cubic centimeter and about 300 microliters per cubic centimeter, between about 200 microliters per cubic centimeter and about 450 microliters per cubic centimeter, between about 250 microliters per cubic centimeter and about 350 microliters per cubic centimeter, between about 300 microliters per cubic centimeter and about 500 microliters). Other ranges are also possible.

The absolute volume of liquid (e.g., a surfactant solution, an antiseptic solution, a buffer, and combinations thereof) included in a wipe or a container may also vary. In some embodiments, the wipe or container contains at least about 100 microliters of liquid, at least about 150 microliters, at least about 200 microliters, at least about 250 microliters, at least about 300 microliters, at least about 350 microliters, at least about 400 microliters, at least about 450 microliters, at least about 500 microliters, at least about 600 microliters, at least about 700 microliters, at least about 800 microliters, at least about 900 microliters of liquid. In certain embodiments, the wipe or container contains less than or equal to about 5 mL, less than or equal to about 3 mL, less than or equal to about 2 mL, less than or equal to about 1 mL, less than or equal to about 700 microliters, less than or equal to about 500 microliters, less than or equal to about 450 microliters, less than or equal to about 400 microliters, less than or equal to about 350 microliters, less than or equal to about 300 microliters, less than or equal to about 250 microliters, less than or equal to about 200 microliters, or less than or equal to about 150 microliters of liquid. Combinations of the above referenced ranges are also possible. Other ranges are also possible.

In some embodiments, each wipe (e.g., the first wipe, the second wipe) may be substantially dry prior to wiping. In other embodiments, the wipe may contain a fluid as described herein. For example, in some embodiments, the wipe contains less than or equal to about 20 microliters, less than or equal to about 10 microliters, less than or equal to about 7 microliters, less than or equal to about 5 microliters, less than or equal to about 3 microliters, or less than or equal to about 1 microliter of fluid per cubic centimeter of wipe. In some embodiments, the wipe contains at least 1 microliter, at least 2 microliters, or at least 5 microliters of fluid per cubic centimeter of wipe. Combinations of the above-referenced ranges are also possible, The wipe (e.g., the first wipe, the second wipe) may comprise or be formed of any suitable material. In certain embodiments, the wipe comprises a material capable of absorbing and retaining a fluid such as a solution comprising a surfactant and/or an antiseptic solution (an absorbent material). In some embodiments, the wipe(s) may include fibers. The fibers may have any suitable average diameter. For example, the average diameter of the fibers may be at least 1 micron, at least about 2 microns, at least about 5 microns, at least about 10 microns, at least about 20 microns, at least about 50 microns, at least about 100 microns, at least about 150 microns, at least about 200 microns, at least about 300 microns, at least about 500 microns, or at least about 700 microns. In certain embodiments, the average diameter of the fibers may be less than or equal to about 1 mm, less than or equal to about 800 microns, less than or equal to about 600 microns, less than or equal to about 400 microns, less than or equal to about 200 microns, less than or equal to about 150 microns, less than or equal to about 100 microns, less than or equal to about 50 microns, less than or equal to about 20 microns, less than or equal to about 10 microns, less than or equal to about 5 microns, or less than or equal to about 2 microns. Combinations of the above-referenced ranges are also possible (e.g., between about 1 micron and about 200 microns, between about 5 microns and about 20 microns, between about 10 microns and about 50 microns, between about 20 microns and about 100 microns, between about 50 microns and about 200 microns). Other ranges are also possible. In certain embodiments, the wipe comprises a non-woven material. In certain embodiments, the wipe comprises a fabric material (e.g., a rough fabric or cloth). In some embodiments, the wipe comprises gauze. Those skilled in the art would be capable of selecting suitable methods for making such wipes including, for example, carding, airlaying, spunlacing, spunlaying, melt-blowing, wetlaying, or the like.

Non-limiting examples of materials suitable for use as a wipe include non-synthetic/natural polymers (e.g., cellulose, regenerated cellulose, cellulose acetate, cotton, wood pulp, hemp) and synthetic polymers (e.g., polyvinyl alcohol, polyester (e.g., polybutylene terephthalate, polybutylene naphthalate, polycaprolactone), polyethylene, polypropylene, acrylic, polyolefin, polyamides (e.g., nylon), rayon, polycarbonates, polyphenylene sulfides, polystyrenes, polybutylene terephthalate, and polyurethanes (e.g., thermoplastic polyurethanes), polymethyl methacrylate, polyaniline, polyaramid (e.g. para-aramid, meta-aramid), polyimide (e.g., polyetherimide), polyether ketone, polyethylene terephthalate, polyolefin, polyacrylics, polyether sulfones, poly(phenylene ether sulfone), polysulfones, polyacrylonitrile, polyvinylidene fluoride, poly(lactic acid), polyphenylene oxide, polypyrrole) and combinations thereof. Fibers of such materials may be used in some instances. In some embodiments, the first wipe and the second wipe comprise the same material. In other embodiments, the first wipe and a second wipe comprise different materials.

In some cases, at least one (e.g., one, two) sides of the wipe has a particular surface roughness. For example, the average root mean squared (RMS) roughness of a surface of the wipe may be at least 1 micron, at least about 2 microns, at least about 5 microns, at least about 10 microns, at least about 25 microns, at least about 40 microns, at least about 60 microns, or at least about 80 microns. In certain embodiments, the average RMS roughness of a surface of the wipe may be less than or equal to about 100 microns, less than or equal to about 80 microns, less than or equal to about 70 microns, less than or equal to about 50 microns, less than or equal to about 40 microns, less than or equal to about 25 microns, less than or equal to about 10 microns, less than or equal to about 5 microns, or less than or equal to about 2 microns. Combinations of the above-referenced ranges are also possible (e.g., between about 1 micron and about 50 microns, between about 2 microns and about 25 microns, between about 5 microns and about 40 microns, between about 25 microns and about 50 microns). Other ranges are also possible. Those skilled in the art would be capable of selecting suitable methods for determining the average RMS roughness of a surface of the wipe including, for example, contact profilometry (e.g., atomic force microscopy).

In some embodiments, the wipe(s) have a particular average thickness. In certain embodiments, the average thickness of the wipe is at least about 100 microns, at least about 200 microns, at least about 500 microns, at least about 1 mm, or at least about 2 mm. In certain embodiments, the wipe has an average thickness of less than or equal to about 5 mm, less than or equal to about 2 mm, less than or equal to about 1 mm, less than or equal to about 500 microns, or less than or equal to about 200 microns. Combinations of the above-referenced ranges are also possible (e.g., between about 100 microns and about 5 mm, between about 200 microns and about 1 mm, between about 500 microns and about 2 mm, between about 1 mm and about 5 mm). Other ranges are also possible.

In certain embodiments, the wipe(s) may be cut to a particular size. For example, the wipe(s) may have a size or area of at least about 0.5 inches×about 0.5 inches, at least about 1 inch×about 1 inch, at least about 2 inches×about 2 inches, or at least about 4 inches×about 4 inches. In some cases, the wipe(s) may have a size or area of less than or equal to about 0.5 inches×about 0.5 inches, less than or equal to about 1 inch×about 1 inch, less than or equal to about 2 inches×about 2 inches, or less than or equal to about 4 inches×about 4 inches. Combinations of the above-referenced ranges are also possible.

The wipe(s) need not necessarily be square in shape and may have any suitable shape (or may be folded to have any suitable shape). For example, in some embodiments, the wipe(s) is square, rectangular, circular, oval, triangular, polygonal, or the like, as defined by the largest cross-sectional area of the wipe(s). Those skilled in the art would understand that the term shape is not limited to its strict geometrical definition, as described in more detail below. In some embodiments, the wipe(s) may be characterized by a largest cross-sectional dimension. For example, in some embodiments, the wipe(s) may have a largest cross-sectional dimension of at least about 0.25 inches, at least about 0.5 inches, at least about 1 inch, at least about 2 inches, at least about 4 inches, at least about 5 inches, or at least about 8 inches. In certain embodiments, the wipe(s) may have a largest cross-sectional dimension of less than or equal to about 10 inches, less than or equal to about 8 inches, less than or equal to about 6 inches, less than or equal to about 5 inches, less than or equal to about 4 inches, less than or equal to about 2 inches, less than or equal to about 1 inch, or less than or equal to about 0.5 inches. Combinations of the above-referenced ranges are also possible (e.g., between about 0.25 inches and about 10 inches, between about 0.25 inches and about 1 inch, between about 0.5 inches and about 2 inches, between about 1 inch and about 5 inches, between about 2 inches and about 8 inches, between about 5 inches and about 10 inches). Other ranges are also possible. In some embodiments, the wipe(s) is folded to have one or more dimensions described above.

In some embodiments, the wipe(s) may be sterilized. Those skilled in the art would be capable of selecting suitable methods for sterilizing the wipes described herein based upon the teachings of the specification including, for example, steam, dry heat, chemical sterilization such as ozone, nonionizing radiation (e.g., ultraviolet light irradiation), and ionizing radiation (e.g., gamma radiation, electron beam processing, x-ray irradiation, or the like). The wipe(s) may be sterilized prior to the absorption of a fluid (e.g., a solution comprising a surfactant, and antiseptic solution). In certain embodiments, the wipe(s) may be sterilized after the absorption of the fluid. In some instances the wipe(s) is sterilized after being placed in a package that contains the wipe.

It should be appreciated that any of the characteristics described herein for a wipe may be independently applicable to the first wipe, the second wipe, to both wipes, and/or to additional wipes. For example, in some embodiments a first wipe comprises a first absorbent material and a second wipe comprises a second absorbent material, while in other embodiments, only one wipe includes an absorbent material.

Referring again to FIG. 1B, in some embodiments, a method described herein comprises third step 130 involving collecting a biological sample after the second wiping step 120. The collection of a biological sample may occur after any suitable period of time after the second wiping step. In some embodiments, the collection of a biological sample occurs less than or equal to about 5 minutes, less than or equal to about 2 minutes, less than or equal to about 60 seconds, less than or equal to about 45 seconds, less than or equal to about 30 seconds, less than or equal to about 15 seconds, or less than or equal to about 10 seconds after the second wiping step. In certain embodiments, the collection of a biological sample occurs at least about 5 seconds, at least about 10 seconds, at least about 15 seconds, at least about 30 seconds, at least about 45 seconds, at least about 60 seconds, at least about 2 minutes, or at least about 5 minutes after the second wiping step. Combinations of the above referenced ranges are also possible (e.g., between 10 seconds and 10 minutes, between 10 seconds and 60 seconds, between 30 seconds and 60 seconds, between 45 seconds and 2 minutes). Other ranges are also possible.

Accordingly, in some embodiments, a method involves collecting a biological sample (e.g., blood sample) from the patient at a collection site, wherein within 1 minute of collecting the (blood) sample, a surface of the collection site was subjected to a first wiping step and a second wiping step. The first wiping step may have involved wiping the surface of the collection site with a first wipe, wherein the first wipe comprises a surfactant, and the second wiping step may have involved wiping at least a portion of the surface of the collection site with a second wipe, wherein the second wipe comprises an antiseptic solution. In some such embodiments, the first and second wipes are different (e.g., they may include different types of components/reagents/solutions, different concentrations of components/reagents, different materials used to form the wipe, different sizes).

In some embodiments, the collection of the biological sample comprises collecting a blood sample from the patient. In certain embodiments, the collection of the biological sample (e.g., blood sample) comprises retrieving the sample using a fluidic device or component, such as a needle, syringe, a "finger stick", a lancet, a capillary (e.g., a tapered capillary), or other suitable component. For example, the biological component may be human skin. A puncture component (e.g., a needle, pin, or other sharp object) may be used to puncture the skin at the collection site prior to or during collection of the biological sample.

In certain embodiments, collection of the biological sample (e.g., blood sample) comprises retrieving the sample using a (micro)fluidic device/(micro)fluidic component that includes at least one channel. In some embodiments, the (micro)fluidic component facilitates transfer of the biological sample from the patient to the at least one channel, such that the biological sample is contained in the channel. In certain embodiments, the (micro)fluidic component may comprise a sampling element that can puncture a biological component (skin), though such a sampling element may not be present in all embodiments. The sampling element may be in the form of a needle or swab, for example. The sampling element may be reversibly or irreversibly attached to a (micro)fluidic component described herein.

As described herein, in some embodiments, a (micro)fluidic component (which may be part of a kit or system described herein) may allow transfer of a biological sample from the patient to a channel within the (micro)fluidic component. In certain embodiments, the (micro)fluidic component is constructed and arranged to be connected to (e.g., inserted into) a microfluidic device including at least one microfluidic channel for analyzing the biological sample. The connection may cause fluidic communication between a channel of the (micro)fluidic component and a channel of the microfluidic device.

In one particular set of embodiments, the (micro)fluidic component is a fluidic connector connecting at least two channels of a microfluidic device. For example, the (micro)fluidic component or fluid connector may comprise a channel including a channel inlet and a channel outlet, wherein upon connection, the channel inlet connects to the outlet of a first microfluidic channel of the microfluidic device to allow fluid communication between the channel of the (micro)fluidic component/fluid connector and the first microfluidic channel, and the channel outlet connects to the inlet of a second microfluidic channel of the microfluidic device to allow fluid communication between the channel and the second microfluidic channel. In some embodiments, the first and second microfluidic channels are not in fluid communication with one another prior to connection by the (micro)fluidic component/fluid connector and/or prior to first use, and at connection/first use, the first and second microfluidic channels are brought into fluid communication with one another. Other configurations are also possible. Examples of (micro)fluidic components, fluidic connectors, and microfluidic devices are provided in International Patent Publication No. WO2008/137008 (International Patent Application Serial No. PCT/US2008/005577), filed May 1, 2008, and entitled "Fluidic Connectors and Microfluidic Systems," which is incorporated herein by reference in its entirety for all purposes.

In some embodiments, a (micro)fluidic component is as an open-ended fluidic device or a fluidic connector includes a volume control element. The volume control element can allow a fluid to fill a portion, but not all, of a channel of the (micro)fluidic component. The volume control element can be used to meter a particular volume of fluid for introduction into a microfluidic device or system as described herein. In one embodiment, a volume control element is a frit, which can be placed inside a channel of a (micro)fluidic component to stop further fluid from being introduced inside the channel after the fluid reaches a particular volume. The volume of fluid (e.g., sample) in the (micro)fluidic component can be defined by the volume of the channel between the entry point (e.g., an inlet) for fluid introduction and the frit; the remaining volume may be occupied by air.

In another embodiment, a volume control element includes one or more metering marks that indicate up to which point(s) a fluid should be introduced into the channel. In yet another embodiment, a volume control element includes a controlled internal volume of the channel, all of which can be filled with a sample. Accordingly, by these and other configurations, the volume of fluid in the channel may be controlled by the user.

In certain embodiments, a channel described herein has a particular average cross-sectional dimension. The "cross-sectional dimension" (e.g., a diameter) of the channel is measured perpendicular to the direction of fluid flow. In some embodiments, the average cross-sectional dimension of the at least one channel is less than or equal to about 2 mm, less than or equal to about 1 mm, less than or equal to about 800 microns, less than or equal to about 600 microns, less than or equal to about 500 microns, less than or equal to about 400 microns, or less than or equal to about 300 microns. In certain embodiments, the average cross-sectional dimension of the at least one channel is greater than or equal to about 250 microns, greater than or equal to about 300 microns, greater than or equal to about 400 microns, greater than or equal to about 500 microns, greater than or equal to about 600 microns, greater than or equal to about 800 microns, or greater than or equal to about 1 mm. Combinations of the above-referenced ranges are also possible (e.g., between about 250 microns and about 2 mm, between about 400 microns and about 1 mm, between about 300 microns and about 600 microns). Other ranges are also possible. The dimensions of the channel may also be chosen, for example, to allow a certain volumetric or linear flowrate of fluid in the channel and/or to hold a certain volume of fluid in the channel. Of course, the number of channels and the shape of the channels can be varied by any method known to those of ordinary skill in the art. In some cases, more than one channel or capillary may be used.

In some embodiments, the at least one channel has a particular length. In some embodiments, the length of the channel is at least about 1 cm, at least about 2 cm, at least about 5 cm, or at least about 7 cm. In certain embodiments, the length of the channel is less than or equal to about 10 cm, less than or equal to about 7 cm, less than or equal to about 5 cm, or less than or equal to about 2 cm. Combinations of the above-referenced ranges are also possible (e.g., between 1 cm and 10 cm). Other ranges are also possible.

The channel can have any cross-sectional shape (circular, oval, triangular, irregular, trapezoidal, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and outlet(s). A channel may also have an aspect ratio (length to average cross sectional dimension) of at least 2:1, more typically at least 3:1, 5:1, or 10:1 or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (e.g., a concave or convex meniscus).

The channel can have any suitable volume. In some embodiments, the volume of the channel may be at least 0.1 microliters, at least 0.5 microliters, at least 1 microliter, at least 2 microliters, at least 5 microliters, at least 7 microliters, at least 10 microliters, at least 12 microliters, at least 15 microliters, at least 20 microliters, at least 30 microliters, or at least 50 microliters. In certain embodiments, the volume of the channel may be less than or equal to 100 microliters, less than or equal to 70 microliters, less than or equal to 50 microliters, less than or equal to 25 microliters, less than or equal to 10 microliters, or less than or equal to 5 microliters. Combinations of the above-referenced ranges are also possible (e.g., between 1 microliter and 10 microliters). Other ranges are also possible.

In certain embodiments, a channel contains a reagent therein (e.g., optionally, for a chemical and/or biological reaction). The reagent may be present in the channel prior to introducing a biological sample into the channel. The reagent may be deposited in fluid and/or in dry form on one or more channel surfaces, and/or within the interior of the channel. The deposited reagent may be associated with a channel in any suitable manner. For example, reagents may be cross-linked, covalently bound, ionically bound, absorbed, adsorbed (physisorbed), or otherwise present on a surface within the fluidic component (e.g., in a channel of the device). In some embodiments, the reagent is a lyophilized reagent, a substantially dry reagent, a labelled reagent, a conditioning reagent, a pH modifier, a viscosity modifier, and/or a surfactant. In certain embodiments, the reagent is a reagent for a chemical and/or biological reaction (e.g., a binding reaction), a dye or otherwise optically detectable substance, or small particles. Non-limiting examples of reagents that may be deposited on a channel surface include anti-coagulants (e.g., heparin, dipyridamole, EDTA), buffers, 2-bromoestradiol, proteins, small molecules, and antibodies including non-labelled and labelled antibodies (e.g., anti-testosterone tracer monoclonal antibodies labeled with metal particles (e.g., nano-gold particles).

As described herein, the methods and articles described herein may be useful in the collection of a biological sample. In certain embodiments, the biological sample comprises a biological fluid. Non-limiting examples of biological fluids include blood, amniotic fluid, bile, breast milk, cerebrospinal fluid, gastric acids, mucus, pus, saliva, urine, lymphatic fluid, and the like. In certain embodiments, the biological sample comprises biological tissue such as bone marrow. In some embodiments, the biological sample comprises blood serum (i.e. a blood sample).

In an exemplary embodiment, the surface of skin may be wiped with a first wipe and a second wipe, and a biological sample may be collected by piercing, with the fluidic component, the location of skin wiped with the first and second wipes such that the fluidic component contacts and extracts the biological sample (e.g., into a device connected and/or configured to connect to the fluidic component). In certain embodiments, the method comprises piercing the location of skin wiped with the first and second wipes such that a droplet of blood forms on the surface of the location of skin, and contacting the fluidic component with the droplet of blood. In certain embodiments, a first droplet of blood formed on the surface of the location of skin is wiped away (e.g., by a third wipe, or with one of the first or second wipes), and a second droplet of blood formed on the surface of the location of skin is contacted with the fluidic component. In some cases, two or more droplets of blood may be formed and removed (e.g., wiped) and a third, fourth, and/or fifth droplet of blood is collected.

In some embodiments, at least the first wipe and the second wipe are provided in a kit. In certain embodiments, the kit comprises the first wipe, the second wipe, and a (micro)fluidic component for collecting a biological sample. Additionally or alternatively to the (micro)fluidic component, in some embodiments the kit includes a device (e.g., a microfluidic device) for analyzing a biological sample. The component(s)/device(s) for collecting and/or analyzing a biological sample are described in more detail herein.

In some embodiments, the first wipe and/or the second wipe are packaged (e.g., stored in a packaging material). For example, the first wipe and/or the second wipe may be disposed or otherwise contained within the package. In some embodiments, the first wipe is disposed within a first package and the second wipe is disposed within a second package separately from the first package. The first package and/or second package may be sealed. In other embodiments, the first and second wipes may be stored together in a single package.

The package may comprise an suitable material. In some embodiments, the package comprises a packaging material impermeable to liquid. For example, in some embodiments, the first wipe is disposed within the first package impermeable to the surfactant solution. In certain embodiments, the second wipe is disposed within the second package impermeable to the antiseptic solution. Non-limiting examples of suitable packaging materials include foil pouches and polymers such as polyethylene terephthalate, polyethylene, or the like. Other materials are also possible. In some embodiments, the packaging material is selected such that the fluid absorbed in the wipe does not substantially exit the packaging.

In some embodiments, the packaging material may be characterized by a water vapor permeability. In some embodiments, the packaging material has a water vapor permeability of less than or equal to about 0.5 gms $H_2O$/100 sq in/24 hours, less than or equal to about 0.1 gms $H_2O$/100 sq in/24 hours, less than or equal to about 0.05 gms $H_2O$/100 sq in/24 hours, less than or equal to about 0.01 gms $H_2O$/100 sq in/24 hours, less than or equal to about 0.005 gms $H_2O$/100 sq in/24 hours, less than or equal to about 0.001 gms $H_2O$/100 sq in/24 hours, less than or equal to about 0.0005 gms $H_2O$/100 sq in/24 hours, or less than or equal to about 0.0001 gms $H_2O$/100 sq in/24 hours. In some embodiments, the packaging material has a water vapor permeability of at least about 0.000001 gms $H_2O$/100 sq in/24 hours, at least about 0.00001 gms $H_2O$/100 sq in/24 hours, at least about 0.0001 gms $H_2O$/100 sq in/24 hours, or at least about 0.001 gms $H_2O$/100 sq in/24 hours. Combinations of the above-referenced ranges are also possible. The measurements may be determined according to the standard ASTM D-1249 at 100 F, 90% relative humidity, RH (37.8 degrees C., 0%).

As noted above, a method described herein may be performed with a patient diagnosed with, known to have, known to be at risk of or developing, or suspected of having a disease or bodily condition, e.g., based on at least one clinical factor and/or other data. The methods described herein may be useful for removing a contaminant at a collection site (e.g., surface of skin) that would otherwise affect (e.g., skew) the results of quantifying a component in the patient sample indicative of or associated with the disease or bodily condition.

In some embodiments, the disease or bodily condition may include, for example, a cancer (e.g., prostate cancer), a hormone deficiency, or a bacterial or viral infection. As such, a method described herein may be performed with a patient diagnosed with, known to have, known to be at risk of or developing, or suspected of having prostate cancer. A biological sample may be obtained for determining the amount of prostate specific antigen, such as free prostate specific antigen, intact prostate specific antigen, total prostate specific antigen, and/or human kallikrein 2 in the sample. In some embodiments, the at least one clinical factor is the patient's age. In some embodiments, the at least one clinical factor is a parameter indicative of the outcome of a digital rectal examination performed on the patient. In some embodiments, the at least one clinical factor is selected from: number of prostate tissue biopsies performed on the patient to date; results of prior prostate tissue biopsies performed on the patient to date; occurrence of any negative biopsy since an initial diagnosis of non-aggressive prostate cancer; occurrence of any negative biopsy in one-year prior to obtaining the blood sample; total number of biopsies since an initial diagnosis of non-aggressive prostate cancer; prostate volume on prior biopsy; number of positive cores on prior biopsy; percent positive cores on prior biopsy; cross-sectional area of cancer in biopsy core sections; maximum cross-sectional area of cancer in any biopsy core sections; PSA density; race of patient; family history of prostate cancer; maximum percent of positive cores from any prior biopsy; and maximum number of positive cores from any prior biopsy. Other clinical factors are also possible.

In some embodiments, after performing wiping and sample collection steps, the amount of PSA present in the biological sample (e.g., fPSA, tPSA, iPSA and/or hK2) may be determined. The amount of PSA(e.g., fPSA, tPSA, iPSA and/or hK2) described herein is determined quantitatively using a Roche Elecsys™ total PSA assay. In some embodiments, a Sangia™ tPSA assay, AuoDELFIA ProSTATUS™ assay, ELISA, or any other suitable assay may be performed. In some embodiments, an assay as described in U.S. Publication No. 2013/0273643, filed Mar. 5, 2013, entitled "Methods and Apparatuses for Predicting Risk of Prostate Cancer and Prostate Gland Volume", which is incorporated herein by reference in its entirety for all purposes, may be performed.

The articles, components, systems, and methods described herein may be combined with those described in International Patent Publication No. WO2005/066613 (International Patent Application Serial No. PCT/US2004/043585), filed Dec. 20, 2004 and entitled "Assay Device and Method"; International Patent Publication No. WO2005/072858 (International Patent Application Serial No. PCT/US2005/003514), filed Jan. 26, 2005 and entitled "Fluid Delivery System and Method"; International Patent Publication No. WO2006/113727 (International Patent Application Serial No. PCT/US06/14583), filed Apr. 19, 2006 and entitled "Fluidic Structures Including Meandering and Wide Channels"; U.S. Pat. No. 8,202,492, issued Jun. 19, 2012 (filed May 1, 2008) and entitled "Fluidic Connectors and Microfluidic Systems" [C1256.70000US01]; U.S. Patent Publication No. 2009/0075390, filed Aug. 22, 2008, entitled "Liquid Containment for Integrated Assays"; U.S. Pat. No. 8,222,049, issued Jul. 17, 2012 (filed Apr. 25, 2008), entitled "Flow Control in Microfluidic Systems"; U.S. Pat. No. 8,221,700, issued Jul. 17, 2012 (filed Feb. 2, 2010), entitled "Structures for Controlling Light Interaction with Microfluidic Devices"; U.S. Patent Publication No. 2010/0158756, filed Dec. 17, 2009, entitled "Reagent Storage in Microfluidic Systems and Related Articles and Methods"; U.S. Patent Publication No. 2011/0120562, filed Nov. 24, 2010, entitled "Fluid Mixing and Delivery in Microfluidic Systems"; U.S. Patent Publication No. 2011/0253224, filed Apr. 15, 2011, entitled "Feedback Control in Microfluidic Systems,"; U.S. Patent Publication No. 2011/0256551, filed Apr. 15, 2011, entitled "Systems and Devices for Analysis of Samples"; U.S. Patent Publication No. 2014/0272935, filed Feb. 7, 2014, entitled "Mixing of Fluids in Fluidic Systems"; U.S. Patent Publication No. 2013/0273643, filed Mar. 5, 2013, entitled "Methods and Apparatuses for Predicting Risk of Prostate Cancer and Prostate Gland Volume"; each of which is incorporated herein by reference in its entirety for all purposes.

EXAMPLES

The following examples are intended to illustrate certain embodiments described herein, including certain aspects of the present invention, but do not exemplify the full scope of the invention.

Example 1

This example demonstrates the measurement of higher than expected tPSA values (i.e., outliers or "fliers") with patient finger-stick samples versus venous samples.

Finger-sticks blood samples were obtained from patients and tested on Sangia™ tPSA cassettes similar to the ones described in U.S. Patent Publication No. 2011/0256551, filed Apr. 15, 2011, entitled "Systems and Devices for Analysis of Samples," (e.g., see FIG. 22 and Example 1) and International Patent Publication No. WO2005/066613 (International Patent Application Serial No. PCT/US2004/043585), filed Dec. 20, 2004 and entitled "Assay Device and Method," which are incorporated herein by reference.

Results using the microfluidic system on the Sangia™ tPSA cassettes were compared to venous blood samples, spun down to plasma, and measured on a reference method, the Roche Elecsys total PSA assay.

In a few instances, there were noted discrepancies between the measured result from the finger-stick and the tPSA result measured from the venipuncture. A total of 257 patients were seen and values for tPSA are shown in Table 1. Multiple finger-stick tests (between 6-12, inclusive) were performed on each patient. Five of the 257 patients had higher measured tPSA values ("fliers") from a subset of the finger-stick measurements on the Sangia™ tPSA kit versus those from venipuncture measurements on the reference assay and versus the other finger-sticks, which matched the reference results.

TABLE 1

| Patient # | Roche tPSA (ng/mL) | # Finger Sticks | # Fliers | Sangia tPSA (ng/mL) | Sangia/ Roche |
|---|---|---|---|---|---|
| 12-21 | 1.27 | 6 | 2 | 4.9 | 4 |
| | | | | 3.43 | 3 |
| 77-12 | 0.679 | 6 | 2 | 8.9 | 13 |
| | | | | 1.4 | 7 |
| 114-18 | 2.04 | 6 | 2 | 9.5 | 5 |
| | | | | 4 | 7 |
| 232-5 | 0.305 | 4 | 2 | 2.9 | 10 |
| | | | | 1 | 3 |
| 448-2 | 0.299 | 2 | 1 | 8.2 | 27 |

These five patients were brought back multiple times to test for "fliers", as shown in Table 2. During the three-month time period, no additional fliers were detected in any of the five patients. For all the visits combined, the chance of "flying" for these 5 of the 257 total patients was 6%. "Flying" (or "fliers"), as used herein, refers to a patient sample having a PSA of greater than 1 ng/mL (as measured by a Sangia™ tPSA cassette as described herein) and the same patient having a finger stick sample concentration of PSA greater than 2 or more times the concentration of total PSA measured in the patient's venous whole blood as determined by the Roche Elecsys™ total PSA assay, all samples collected at the same visit. A "flier" generally refers to an outlier whose total PSA measured by a sample obtained by a finger-stick is significantly different from the total PSA measured by a venous whole blood sample.

Example 2

This example demonstrates the determination of a potential source of variance in PSA recovery between finger-stick and venous samples draw.

Finger-stick and venous samples both measured on Sangia™ tPSA, as described in Example 1. For patients for whom there was a discrepancy between the Sangia™ tPSA finger-stick test and the reference method, the Sangia™ tPSA tests were also performed using EDTA whole blood samples obtained from venipuncture from the same patients. The venous results tested on the Sangia™ tPSA assay corresponded to the venous results tested on the reference method. These results demonstrated that the source of the discrepancy was associated with the collection of blood at the finger, and not an interference between a component in circulation in whole blood and the assay itself.

In a subset of patients (37 patient visits) finger-stick samples were collected and tested on multiple platforms. Finger-stick samples were collected and tested on the Sangia™ tPSA assay. Additional finger-stick samples were collected, diluted, spun down, and tested on an in-house ELISA, the Roche-Elecsys™ tPSA, and the AuoDELFIA ProSTATUS™ total and free PSA assay. In addition, venous EDTA samples were collected and tested on each system. For the finger-stick samples, one hand was cleaned thoroughly with soap and water and with baby wipes (Seventh Generation, Free & Clear Baby Wipes). The other hand was not cleaned with baby wipes (and those fingers considered "dirty"). For each finger-stick ("dirty" and "clean") was preceded with a standard alcohol wipe of that finger.

A total of 34 patients showed consistent PSA recoveries between venous blood and finger-stick blood; see Table 3 below for patient 77-15. One patient showed inconsistent recovery in PSA between venous blood and finger-stick blood, see Table 4 below with patient 112-11.

Table 3 shows results for a patient who had previously (once) demonstrated a variance in results between finger-stick and venous EDTA results but did not on this visit. As can be seen, there was no difference between the finger-stick and venous results on any platform, nor was there a difference between "dirty" and "clean" fingers.

TABLE 3

| 77-15 | # | Sangia tPSA (ng/mL) | ELISA (ng/mL) | Roche tPSA (ng/mL) | ProSTATUS tPSA (ng/mL) | ProSTATUS fPSA (ng/mL) | fPSA/ tPSA |
|---|---|---|---|---|---|---|---|
| dirty fingers | 1 | 0.49 | 0.21 | 0.36 | 0.40 | 0.10 | 0.3 |
| | 2 | 0.54 | 0.21 | 0.33 | 0.29 | 0.08 | 0.3 |
| | 3 | 0.51 | 0.20 | 0.35 | 0.35 | 0.09 | 0.3 |

TABLE 3-continued

| 77-15 | # | Sangia tPSA (ng/mL) | ELISA (ng/mL) | Roche tPSA (ng/mL) | ProSTATUS tPSA (ng/mL) | ProSTATUS fPSA (ng/mL) | fPSA/ tPSA |
|---|---|---|---|---|---|---|---|
| Avg. dirty finger | | 0.5 | 0.2 | 0.3 | 0.3 | 0.1 | 0.3 |
| clean | 4 | 0.59 | 0.19 | 0.34 | 0.35 | 0.07 | 0.2 |
| fingers | 5 | 0.56 | 0.17 | 0.34 | 0.41 | 0.10 | 0.2 |
| | 6 | 0.49 | 0.20 | 0.28 | 0.27 | 0.09 | 0.3 |
| Avg. clean finger | | 0.5 | 0.2 | 0.3 | 0.3 | 0.1 | 0.3 |
| venous | 1 | 0.5 | 0.14 | 0.32 | 0.27 | 0.09 | 0.27 |
| EDTA | 2 | 0.52 | 0.14 | | 0.24 | 0.11 | 0.36 |
| | 3 | 0.48 | 0.17 | | 0.22 | 0.09 | 0.30 |
| Avg. EDTA | | 0.50 | 0.15 | 0.32 | 0.24 | 0.10 | 0.31 |
| Avg. dirty/clean | | 1 | 1 | 1 | 1 | 1 | 1 |
| Avg. finger/EDTA | | 1 | 1 | 1 | 1 | 1 | 1 |

Table 4 shows results for a patient (#112) who has a history of demonstrated a variance in results between finger-stick and venous EDTA results and showed a variance again on this visit. As can be seen, each platform measured a difference between the finger-stick and the venous sample. This data demonstrates that the source of the inconsistent PSA recovery in finger-stick may be platform independent. Also, there was a measureable difference between clean and dirty fingers, indicating that the contaminant could be potentially removed by some sort of cleaning. Finally, the ratio of free-PSA to total-PSA from the finger-sticks was 0.8:1 versus 0.3:1 in the venous sample. This indicates that the contaminant (from the finger-stick sample) may be homologous with free-PSA. Without wishing to be bound by theory, since PSA can be found endogenously only in venous blood (typically in the form of complexed PSA) and seminal fluids (typically in the form of free PSA), it is likely that the patient had one of these forms of PSA present on his finger. However, a ratio of 0.8:1 free-PSA to total-PSA obtained from a finger-stick (e.g., relatively higher amounts of free-PSA compared to that from a venous blood sample, which had a ratio of 0.3:1) suggests that the contaminant was primarily composed of free-PSA (which is found in seminal fluid).

To confirm that the contaminant was on the finger surface, a technique was used to measure by using the following steps:
1. Fingers were tested upon patient's arrival at the clinic, with no initial hand-washing.
2. A 25 μL drop of PBSB1 buffer (phosphate buffer saline with 1% bovine serum albumin) was applied to the finger with a pipette. The drop of buffer was allowed to remain on the finger for a total of 20 seconds. After the first 10 seconds it was mixed by pulling it into and out of the pipette 5 times.
3. The drop was removed from the finger and diluted into 200 μL of PBSB1 buffer measured with the AutoDEL-FIA ProStatus PSA free/total kit ("dirty fingers"). The concentration of the buffer drop was calculated accounting for dilution.
4. This was repeated for six fingers.
5. Hands were washed using soap and hot water.
6. The application, mixing, and removal of a buffer droplet was repeated for six fingers and the droplets diluted and measured with the AutoDELFIA ProStatus PSA free/total kit ("clean fingers").

As can be seen in Table 5, for the patient (#112) who generally presents with higher than expected tPSA measurements from finger-sticks ("fliers"), a measurable amount of contaminant was detected on his fingers. This contaminate was nearly all free-PSA (or homologous with free-PSA). The concentration of contaminant was reduced, but not eliminated, by washing with soap and water.

TABLE 4

| 112-11 | # | Sangia tPSA (ng/mL) | ELISA (ng/mL) | Roche tPSA (ng/mL) | ProSTATUS tPSA (ng/mL) | ProSTATUS fPSA (ng/mL) | fPSA/ tPSA |
|---|---|---|---|---|---|---|---|
| dirty | 1 | 3.6 | 4.5 | 2.7 | 6.5 | 5.06 | 0.8 |
| fingers | 2 | 1.6 | 25.1 | 6.5 | 44.0 | 36.19 | 0.8 |
| | 3 | 4.0 | 13.6 | 18.6 | 20.7 | 15.50 | 0.7 |
| Avg. dirty finger | | 3.1 | 14.4 | 9.3 | 23.7 | 18.9 | 0.8 |
| clean | 4 | 1.2 | 2.8 | 1.6 | 4.3 | 3.25 | 0.8 |
| fingers | 5 | | 1.7 | 1.9 | 3.4 | 2.50 | 0.7 |
| | 6 | 2.1 | 4.4 | 9.0 | 6.7 | 5.36 | 0.8 |
| Avg. clean finger | | 1.6 | 2.9 | 4.2 | 4.8 | 3.7 | 0.8 |
| venous | 1 | 0.57 | 0.11 | 0.43 | 0.40 | 0.11 | 0.27 |
| EDTA | 2 | 0.65 | 0.12 | 0.42 | 0.36 | 0.13 | 0.36 |
| | 3 | 0.68 | 0.13 | 0.43 | 0.35 | 0.11 | 0.30 |
| Avg. EDTA | | 0.63 | 0.12 | 0.43 | 0.37 | 0.12 | 0.31 |
| Avg. dirty/clean | | 2 | 5 | 2 | 5 | 5 | 1 |
| Avg. finger/EDTA | | 4 | 72 | 16 | 38 | 98 | 2 |

TABLE 5

| 112-12 | # | ProSTATUS tPSA (ng/mL) | ProSTATUS fPSA (ng/mL) | fPSA/ tPSA |
|---|---|---|---|---|
| dirty | 1 | 27.3 | 26.90 | 1.0 |
| fingers | 2 | 31.5 | 31.20 | 1.0 |

TABLE 5-continued

| 112-12 | # | ProSTATUS tPSA (ng/mL) | ProSTATUS fPSA (ng/mL) | fPSA/tPSA |
|---|---|---|---|---|
| | 3 | 41.2 | 41.30 | 1.0 |
| | 4 | 75.6 | 79.40 | 1.1 |
| | 5 | 49.6 | 51.10 | 1.0 |
| | 6 | 21.7 | 21.70 | 1.0 |
| Avg. dirty finger | | 41.2 | 41.9 | 1.0 |
| clean | 1 | 18.5 | 18.20 | 1.0 |
| fingers | 2 | 11.4 | 11.30 | 1.0 |
| | 3 | 3.9 | 3.60 | 0.9 |
| | 4 | 8.0 | 5.00 | 0.6 |
| | 5 | 15.2 | 15.10 | 1.0 |
| | 6 | 3.1 | 3.30 | 1.1 |
| Avg. clean finger | | 10.0 | 9.4 | 0.9 |
| Avg. dirty/clean | | 4 | 4 | |

From these tests it appears that the source of variation between finger-stick and venous testing may not be due to the deficiency of any particular assay, but instead may be due to a contaminant on the finger such as free-PSA. An alcohol wipe was not sufficient to remove this contaminant. A commercial baby wipe was also not sufficient to remove this contaminant. The concentration of this contaminant can be reduced by washing with soap and hot water.

Example 3

This example demonstrates the testing of a variety of wipes to remove contaminants from the finger. These included an additional alcohol pad, adhesive remover, castile soap, povidone-iodine, chlorhexidine, 5% (wt:vol) SDS, 5% urea, and Benzalkonium chloride (BZK). The selection included commercially available wipes (for medical application) as well as wipes formulated in-house when commercial products were not available.

Testing of each wipe consisted of the following steps:
1. A solution containing free-PSA was applied to the fingers and allowed to dry.
2. The finger was wiped with selected product to be tested (e.g., a first wipe).
3. The finger was wiped again with the standard alcohol pad (e.g., a second wipe).
4. A 25 µL drop of PBSB1 buffer was applied to the finger with a pipette. The drop of buffer was allowed to remain on the finger for 20 seconds. After the first 10 seconds it was mixed by pulling it into and out of the pipette 5 times.
5. The drop was removed from the finger diluted into 200 µL of PBSB1 buffer measured on the AutoDELFIA ProStatus PSA free/total kit. The concentration of the buffer drop was calculated accounting for dilution.

The results are shown in Table 6.

TABLE 6

| | Avg. pre-wipe PSA (ng/mL) | Avg. post-wipe PSA (ng/mL) | Max post wipe PSA (ng/mL) | Avg. PSA ratio Post/Pre |
|---|---|---|---|---|
| Povidone-Iodine | 14.7 | 0.18 | 0.44 | 1% |
| 2% Chlorhexidine | 12.6 | 0.12 | 1.0 | 1% |
| SDS | 16.3 | 0.21 | 0.67 | 1% |
| 5% Urea | 15.2 | 0.32 | 1.9 | 2% |
| Nothing (alcohol pad alone) | 13.6 | 6.1 | 14.7 | 59% |

This model system indicate that the use of a wipe before the use of the alcohol pad resulted in an approximately 100 times reduction in detected PSA.

Example 4

This example demonstrates the procedure for wiping a finger prior to blood collection.

Each wipe was tested to determine whether it would affect blood collection for the Sangia™ tPSA assay, as described in Example 1.

In the first set of tests, the hands were washed with soap and water. A finger was then wiped with selected product to be tested. The Sangia™ SOP finger-stick procedure was followed to collect a droplet and test it using the Sangia™ tPSA assay. A finger-stick was performed to create a droplet of blood. The first two droplets were wiped away, and a third droplet created. This droplet was collected using the blood collector contained in a Sangia™ tPSA kit, and tested on the Sangia™ tPSA assay on the Claros 1 analyzer, as described in more detail in U.S. Pat. No. 8,932,523, issued Jan. 13, 2015, entitled "Systems and Devices for Analysis of Samples," which is incorporated herein by reference in its entirety for all purposes.

For wipes with absorbed SDS: a blood droplet created after the SDS wipe was difficult to collect using a fluidic device (blood collector). The detergent left a hydrophilic layer on the surface of the finger onto which the blood droplet spread (instead of maintaining an easy-to-collect droplet shape).

For wipes with absorbed povidone-iodine: The blood droplet created after a povidone-iodine wipe was easy to collect. The procedure left a brown color on the finger easy to remove with alcohol or soap and water afterwards.

For wipes absorbed with castile soap: similar to SDS, a blood drop created after the Castile soap wipe was difficult to collect due to spreading on the finger.

For wipes absorbed with chlorhexidine: The procedure left a film that took a relatively long time to air-dry. The blood droplet spread, similar to SDS and castile soap, but to a lesser extent.

For wipes absorbed with benzalkonium chloride (BZK): A blood droplet created after the BZK wipe was easy to collect.

For wipes absorbed with 5% urea: A blood droplet created after the 5% urea wipe demonstrated some spreading, but could still be collected.

In the second set of tests, the hands were washed with soap and water. Then, a finger was wiped with selected product to be tested (a first wipe). The finger was wiped again with the standard alcohol pad (a second wipe). Sangia™ SOP finger-stick procedure was followed to collect a droplet and test it using the Sangia™ tPSA assay.

Using a secondary wipe with alcohol pad eliminated the difficulty in collecting a droplet of blood from a finger previously wiped with SDS. Using a secondary wipe with alcohol pad removed the color from the povidone-iodine wipe. Using a secondary wipe with alcohol pad eliminated the any difficulty in collecting a droplet of blood from a finger previously wiped with Castile soap, BZK, chlorhexidine, and 5% urea.

Example 5

This example demonstrates the results for removing free-PSA by various wipes.

Figure 2:
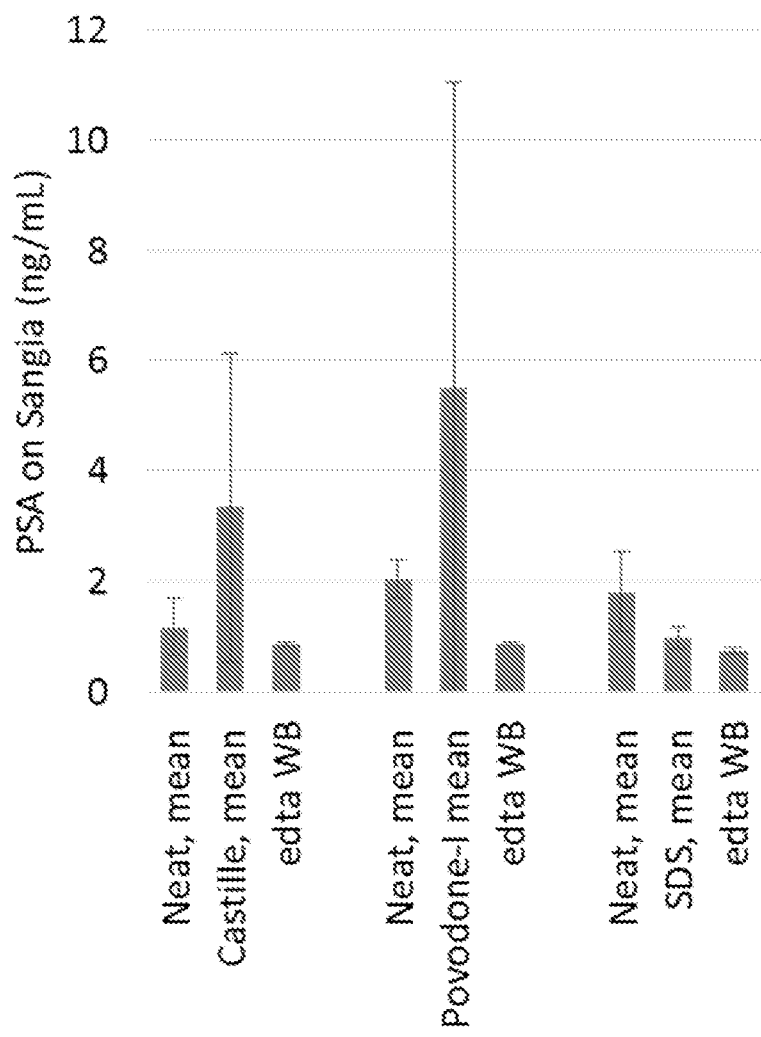
FIG. 2 is a plot of PSA (in ng/mL) measured by a tPSA assay performed after various wiping procedures, according to one set of embodiments.

Each wipe was tested using the Sangia™ tPSA assay, as described in Example 1. Testing of each wipe consisted of the following steps, each on 4 fingers:
1. Seminal fluid (containing free-PSA) was applied to the fingers and allowed to dry for five minutes, before washing with soap and water.
2. After 30-90 minutes, the hands were washed again with soap and water.
3. The finger was wiped with the standard alcohol pad.
4. Sangia™ SOP finger-stick procedure was followed to collect a droplet and test it using the Sangia™ tPSA assay.
5. A finger was wiped with selected product to be tested.
6. The finger was wiped again with the standard alcohol pad.
7. Sangia™ SOP finger-stick procedure was followed to collect a droplet and test it using the Sangia™ tPSA assay.
8. An EDTA whole blood sample was collected from a venipuncture and tested using a reference assay Results for measured tPSA values for various wipes are shown in Table 7 and FIG. 2.

TABLE 7

| Wipe | Finger | | | | | |
|---|---|---|---|---|---|---|
| | #1 | #2 | #3 | #4 | Mean | SD |
| Castile wipe | | | | | | |
| Alcohol pad only result (ng/mL) | 1.96 | 0.95 | 0.81 | 0.99 | 1.18 | 0.53 |
| Post Castile wipe (ng/mL) | 1.04 | 7.2 | 1.51 | 3.61 | 3.34 | 2.81 |
| edta WB (ng/mL) | 0.81 | 0.86 | 0.89 | | 0.85 | 0.04 |
| Povidone Iodine wipe | | | | | | |
| Alcohol pad only result (ng/mL) | 1.85 | 1.67 | 2.18 | 2.49 | 2.05 | 0.36 |
| Post PI wipe (ng/mL) | 13.05 | 6.33 | 1.26 | 1.44 | 5.52 | 5.54 |
| edta WB (ng/mL) | 0.9 | 0.84 | 0.88 | | 0.87 | 0.03 |
| SDS wipe | | | | | | |
| Alcohol pad only result (ng/mL) | 1.23 | 1.25 | 2.02 | 2.75 | 1.81 | 0.73 |
| Post SDS wipe (ng/mL) | 0.72 | 1.01 | 1.19 | 1 | 0.98 | 0.19 |
| edta WB (ng/mL) | 0.8 | 0.7 | | | 0.75 | 0.07 |

The SDS wipe demonstrated the best reduction in measured PSA on the finger, with the measured tPSA falling within the range of the tPSA measured from a venipuncture (see edta WB values).

Since SDS is a soap, castile soap was included in the data provided as a comparison. It is believed that the contaminant is a protein (freePSA or similar/homologous to freePSA). Without wishing to be bound by any theory, since detergents can solubilize and denature proteins, and 5% SDS is a strong detergent, SDS may be able to reduce the measured PSA on the finger. Castile soap is a weak detergent and therefore application may solubilize some of the contaminant but not remove or denature it, thus resulting in an increased signal after the wiping step. Povidone iodine may only wet the contaminant, making it easier to mix with a blood droplet.

Example 6

This example demonstrates the use of various materials for the wipes.

Since wiping involves mechanical cleansing as well as chemical cleansing, a rough gauze pad was selected for use with SDS. This custom wipe was assembled internally using a 2"×1" wipe (commercial gauze) folded in half to form a 1"×1" wipe, which included a solution of 5% SDS in water.

SDS generally foams up during application with a gauze. Too much foam may not be adequately cleaned with an alcohol wipe. To select suitable amounts of SDS solution to add to the gauze pad, multiple foil pouches containing the gauze pad and five volumes of SDS were prepared. Five separate operators tested five such preparations each on two fingers (ten fingers total) of patients to determine which pad had sufficient surfactant to cover the finger-stick area and also be easily wiped away by an alcohol wipe. A total of five patients were tested.

The selected configuration was the Fisherbrand Non-Sterile Cotton Gauze sponges (Cat. No. 22-362-178), cut to 1"×1" size, in 300 µL volume of 5% SDS solution.

Example 7

This example demonstrates the use of a surfactant-containing wipe (a first wipe) followed by an antiseptic-containing wipe (a second wipe) for removal of free-PSA prior to a finger-stick.

Two separate operators performed the test. A solution containing free-PSA was applied to the fingers and allowed to dry. The hands were washed with soap and water. Four collection sites on four fingers were wiped with the standard alcohol pad. Sangia™ SOP finger-stick procedure was followed to collect a droplet and test it using the Sangia™ tPSA assay, as described in Example 1.

The same four collection sites were then wiped with the surfactant wipe (first wipe), followed by the alcohol pad (second wipe). Sangia™ SOP finger-stick procedure was again followed to collect a droplet and test it using the Sangia™ tPSA assay. Venous blood measured with the Sangia™ tPSA assay was used as the reference. Bias of finger-stick results versus the reference were calculated for both before and after use of the surfactant wipe.

Figure 3:
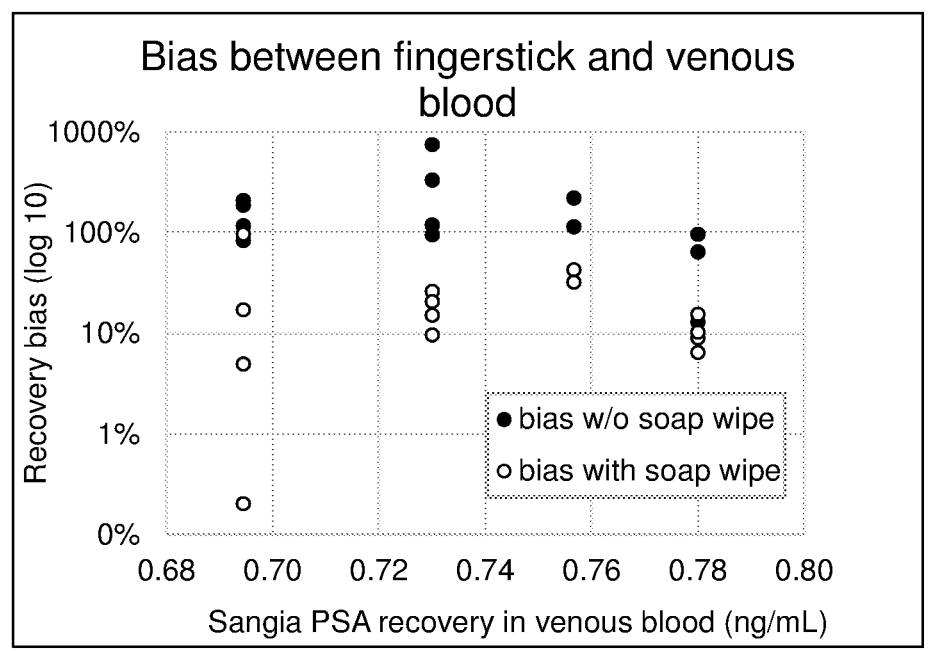
FIG. 3 is a plot of bias between finger-stick blood samples (collected on finger contaminated with PSA) and venous blood samples as a function of PSA recovery (in ng/mL), according to one set of embodiments.

FIG. 3 shows the recovery bias versus Sangia™ tPSA recovery in venous blood. The mean bias (FS to venous WB) without the surfactant wipe was 168% versus 22% with usage of the surfactant wipe.

Several patients were invited to the clinic for finger-sticks and tested as follows: The hands were washed with soap and water. Two fingers were selected. Each was wiped with an alcohol pad and tested using the Sangia™ SOP finger-stick procedure to obtain a droplet of blood and test using the Sangia™ tPSA assay on the Claros 1 analzyer. If either result was considered high (a "high-flier," where the result was high relative to the other finger, measured by a test of EDTA whole blood from a venipuncture, or compared to a previous results from the patient), two additional fingers were selected for testing. Each finger was wiped with a surfactant wipe, followed by an alcohol wipe, followed by the Sangia™ SOP finger-stick procedure and test described in Example 4.

The wipe used in this example was based on a smooth finish wipe loaded with 5% SDS, which may have similar or reduced capability to clean off PSA from the finger relative to a custom wipe in Example 6.

A total of 91 patients were tested, with 3 patients (one of whom was patient 112) presenting with discordant results. Results are shown in Table 8.

The surfactant wipe eliminated the discordants. The surfactant wipe eliminated some, but not all of the fliers from patient 112, who is considered to be an extreme outlier (in regards to contamination) among all the patients tested previously with the Sangia™ tPSA assay, as shown in Table 9.

TABLE 8

| Patient ID | Roche tPSA venous plasma (ng/mL) | Sangia ™ tPSA from venous blood (ng/mL) | Sangia ™ tPSA from FS w/o surfactant wipe (ng/mL) | Sangia ™ tPSA from FS with surfactant wipe (ng/mL) |
|---|---|---|---|---|
| 223 | 0.51 | 0.60, 0.65 | >16, 1.56 | 0.58, 0.56 |
| 260 | 0.64 | 0.60, 0.51, 0.45 | 0.52, 1.22 | 0.47, 0.65 |

TABLE 9

| Patient ID | Roche tPSA venous plasma (ng/mL) | Sangia ™ tPSA from venous blood (ng/mL) | Sangia ™ tPSA from FS w/o surfactant wipe (ng/mL) | Sangia ™ tPSA from FS with surfactant wipe (ng/mL) |
|---|---|---|---|---|
| 112 | 0.60 | 0.72, 0.8, 0.8 | >16, >16, >16 | 11.8, 2.0, >16, 1.6 |

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Any terms as used herein related to shape, orientation, alignment, and/or geometric relationship of or between, for example, one or more articles, structures, forces, fields, flows, directions/trajectories, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, circular/circle, rectangular/rectangle, triangular/triangle, cylindrical/cylinder, elipitical/elipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/tangential, etc.; direction—such as, north, south, east, west, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described. As another example, two or more fabricated articles that would described herein as being "aligned" would not require such articles to have faces or sides that are perfectly aligned (indeed, such an article can only exist as a mathematical abstraction), but rather, the arrangement of such articles should be interpreted as approximating "aligned," as defined mathematically, to an extent typically achievable and achieved for the recited fabrication technique as would be understood by those skilled in the art or as specifically described.

The invention claimed is:

1. A method for determining an amount of PSA protein in a patient, comprising:
   wiping a surface of skin with a first wipe, the first wipe comprising a solution comprising a surfactant, wherein the surfactant is present in the solution in an amount of between about 0.1 wt % and about 15 wt % of the solution; and
   wiping at least a portion of the surface with a second wipe, the second wipe comprising an antiseptic solution, wherein the first and second wipes are different,
   wherein the step of wiping at least a portion of the surface with the second wipe occurs after less than or equal to about 60 seconds of contacting the surface with the first wipe;
   removing at least 95% of any PSA protein from the surface of the skin after the first and second wiping steps compared to an amount of any PSA protein present on the surface before the first and second wiping steps, as determined by a tPSA assay;
   forming a first blood droplet on the surface of the skin after the step of wiping at least a portion of the surface with the second wipe;
   wiping away the first blood droplet with the first wipe, the second wipe, or a third wipe;
   forming a second blood droplet on the surface of the skin after the step of wiping away the first blood droplet; and
   determining an amount of any PSA protein present in a blood sample of the patient.

2. A method as in claim 1, wherein the second wiping step occurs after less than or equal to about 30 seconds of the first wiping step, and wherein the method comprises collecting a blood sample from the patient at a collection site, wherein collecting the blood sample occurs after less than or equal to about 45 seconds of the second wiping step.

3. A method as in claim 1, wherein the any PSA protein is free PSA, or a protein homologous with free-PSA.

4. A method as in claim 1, wherein the step of wiping at least a portion of the surface of the skin with the second wipe occurs between about 1 second and about 20 seconds of contacting the surface with the first wipe.

5. A method as in claim 1, wherein wiping with the second wipe substantially removes any surfactant present on the surface.

6. A method as in claim 1, comprising collecting the blood sample from the patient.

7. A method as in claim 6, wherein collecting the blood sample comprises retrieving the blood sample using a fluidic component.

8. A method as in claim 7, wherein the fluidic component comprises at least one channel.

9. A method as in claim 8, wherein the at least one channel has an average cross-sectional dimension of less than or equal to about 2 mm.

10. A method as in claim 8, wherein the at least one channel has an average cross-sectional dimension of between about 300 microns and about 600 microns.

11. A method as in claim 8, wherein the at least one channel has a length of between 1 cm and 10 cm.

12. A method as in claim 1, wherein the surfactant is an anionic surfactant.

13. A method as in claim 1, wherein the surfactant is sodium dodecyl sulfate.

14. A method as in claim 1, wherein the first wipe and/or the second wipe is sterilized.

15. A method as in claim 1, wherein the antiseptic solution comprises an alcohol.

16. A method as in claim 15, wherein the alcohol is isopropyl alcohol.

17. A method as in claim 15, wherein the alcohol is present in the antiseptic solution in an amount ranging between about 30 vol % and about 80 vol % of the antiseptic solution.

18. A method as in claim 1, wherein the antiseptic solution contains an antiseptic in an amount of at least 0.01 wt % and less than or equal to about 7 wt % versus the total weight of the solution.

19. A method as in claim 1, comprising retrieving the blood sample from either the second blood droplet or a third droplet optionally formed on the surface of the skin after wiping the second blood droplet away, by contacting a fluidic component to at least a portion of the second droplet or the third droplet.

20. A method as in claim 19, further comprising transferring the blood sample into a channel within a fluidic component, wherein the fluidic component is arranged to be connected to a fluidic device, the fluidic device comprising at least one microfluidic channel for analyzing the blood sample.

21. A method as in claim 1, comprising wiping the second blood droplet away, forming a third droplet on the surface of the skin after the step of wiping away the second blood droplet, retrieving the blood sample from the third droplet formed on the surface of the skin by contacting a fluidic component to at least a portion of the third droplet, connecting the fluidic component to a fluidic device comprising at least one microfluidic channel for analyzing the blood sample, and transferring at least a portion of the blood sample from the fluidic component to the fluidic device.

22. A method as in claim 1, wherein the first wipe comprises a compound or component capable of denaturing any PSA protein.

23. A method as in claim 1, wherein the surfactant is capable of denaturing any PSA protein.

\* \* \* \* \*

UNITED STATES PATENT AND TRADEMARK OFFICE
CERTIFICATE OF CORRECTION

| | |
|---|---|
| PATENT NO. | : 11,013,576 B2 |
| APPLICATION NO. | : 15/535665 |
| DATED | : May 25, 2021 |
| INVENTOR(S) | : Jason Taylor et al. |

It is certified that error appears in the above-identified patent and that said Letters Patent is hereby corrected as shown below:

On the Title Page

Item (54) and in the Specification, Column 1, Lines 1-3, the title is hereby corrected as shown below:
ARTICLES AND METHODS FOR PREPARING A SURFACE FOR OBTAINING A PATIENT SAMPLE

Item (72), the address of inventor David Steinmiller is hereby corrected as shown below:
(72) Inventors: Jason Taylor, Windham, NEW HAMPSHIRE (US);
David Steinmiller, Half Moon Bay, CALIFORNIA (US);
Hardeep Singh, Arlington, MASSACHUSETTS (US);
Rebecca Wagner, Boulder, COLORADO (US);
Gary J. Fagan, Marblehead, MASSACHUSETTS (US);
Vincent Linder, Tewksbury, MASSACHUSETTS (US)

Signed and Sealed this
Twentieth Day of December, 2022

Katherine Kelly Vidal
*Director of the United States Patent and Trademark Office*